US006887983B2

(12) United States Patent
Tanzi et al.

(10) Patent No.: US 6,887,983 B2
(45) Date of Patent: May 3, 2005

(54) PURIFIED 20 KDA PRESENILIN 2 C-TERMINAL FRAGMENT AND METHODS OF SCREENING FOR COMPOUNDS THAT INHIBIT PROTEOLYSIS OF PRESENILIN 2

(75) Inventors: Rudolph E. Tanzi, Hull, MA (US); Tae-Wan Kim, Waltham, MA (US)

(73) Assignee: The General Hospital Corporation, Boston, MA (US)

( * ) Notice: Subject to any disclaimer, the term of this patent is extended or adjusted under 35 U.S.C. 154(b) by 113 days.

(21) Appl. No.: 09/065,902

(22) Filed: Apr. 24, 1998

(65) Prior Publication Data

US 2002/0086444 A1 Jul. 4, 2002

Related U.S. Application Data

(60) Provisional application No. 60/044,262, filed on Apr. 24, 1997.

(51) Int. Cl.[7] .............................................. C07K 16/00
(52) U.S. Cl. ...................... 530/388.85; 435/4; 435/7.1; 435/975
(58) Field of Search ............................ 435/4, 7.1, 975; 530/387.85, 387.1, 388.1, 388.85; 436/536, 548

(56) References Cited

U.S. PATENT DOCUMENTS 4,116,776 A * 9/1978 Dalbow et al. .......... 195/103.7

OTHER PUBLICATIONS

Vito et al., J. Biol. Chem. 271(49):31025–31028, Dec. 1996.*
Janeway and Travers, Immunobiology, New York, Current Biology, 1997.*
Miller et al. , Annals New York Acad. Sci., 696:133–148, 1993.*
Kim et al. Journal of Neurobiology of Aging. vol. 17, p. 5155, 1996.*
Tanzi, R.E. et al., "The Presenilin Genes and Their Role in Early–Onset Familial Alzheimer's Disease," *Alzheimer's Dis. Rev.* 1:90–98 (1996).
Borchelt, D.R., et al., "Familial Alzheimer's Disease–Linked Presenilin 1 Variants Elevate Aβ1–42/1–40 Ratio In Vitro and In Vivo," *Neuron* 17:1005–1013 (Nov. 1996).
Bush, A.I., et al., "An Abnormality of Plasma Amyloid Protein Precursor in Alzheimer's Disease," *Annals of Neurology* 32:57–65 (1992).
Chinnaiyan, A.M., and Dixit, V.M., "The cell–death machine," *Current Biology* 6:555–562 (May 1996).
Ciechanover, A., "The Ubiquitin–Proteasome Proteolytic Pathway," *Cell* 79:13–21 (1994).
Citron, M., et al., "Mutant presenilins of Alzheimer's disease increase production of 42–residue amyloid β–protein in both transfected cells and transgenic mice," *Nature Medicine* 3:67–72 (Jan. 1997).

Cook, D.G., et al., "Expresison and analysis of presenilin 1 in a human neuronal system: Localization in cell bodies and dendrites," *Proc. Natl Acad. Sci. USA* 93:9223–9228 (Aug. 1996).
Cotman, C.W., and Anderson, A.J., "A Potential Role for Apoptosis in Neurodegeneration and Alzheimer's Disease," *Molecular Neurobiology* 10:19–45 (1995).
Deng, G., et al., "Alzheimer–associated presenilin–2 confers increased sensitivity to apoptosis in PC12 cells," *FEBS Letters* 397:50–54 (Nov. 1996).
Doan, A., et al., "Protein Topology of Presenilin 1," *Neuron* 17:1023–1030 (Nov. 1996).
Duff, K., et al., "Increased amyloid–β42(43) in brains of mice expressing mutant presenilin 1," *Nature* 383:710–713 (Oct. 1996).
Fenteany, G., et al., "Inhibition of Proteasome Activities and Subunit–Specific Amino–Terminal Threonine Modification by Lactacystin," *Science* 268:726–731 (1995).
Finley, D., and Chau, V., "Ubiquitination," *Annu. Rev. Cell Biol.* 7:25–69 (1991).
Forloni, G., et al., "Apoptosis mediated neurotoxicity induced by chronic application of β amyloid fragment 25–35," *NeuroReport* 4:523–526 (1993).
Guo, Q., et al., "Alzheimer's PS–1 mutation perturbs calcium homeostasis and sensitizes PC12 cells to death induced by amyloid β–peptide," *NeuroReport* 8:379–383 (Dec. 1996).
Goldberg, Y.P., et al., "Cleavage of huntingtin by apopain, a proapoptotic cysteine protease, is modulated by the polyglutamine tract," *Nature Genetics* 13:442–449 (Aug. 1996).
Gossen, M., and Bujard, H., "Tight control of gene expression in mammalian cells by tetracycline–responsive promoters," *Proc. Natl. Acad. Sci. USA* 89:5547–5551 (1992).
Hochstrasser, M., "Ubiquitin, proteasomes, and the regulation of intracellular protein degradation," *Curr. Opin. Cell Biol.* 7:215–223 (1995).
Hochstrasser, M., "Protein Degradation or Regulation Ub the Judge," *Cell* 84:813–815 (Mar. 1996).

(Continued)

Primary Examiner—Patrick J. Nolan
(74) Attorney, Agent, or Firm—Sterne Kessler Goldstein & Fox, PLLC

(57) ABSTRACT

The present invention relates, in general, to presenilin 2 proteolytic fragments. In particular, the present invention relates to a purified 20 kDa presenilin 2 C-terminal fragment (PS2-CTF); purified nucleic acid molecules coding for the 20 kDa PS2-CTF protein; cells containing the nucleic acid molecules; non-human organisms containing the nucleic acid molecule; antibodies having specific binding affinity to the 20 kDa PS2-CTF; hybridomas containing the antibodies; methods of detecting 20 kDa PS2-CTF in a sample; diagnostic kits; methods for screening compounds that inhibit proteolytic processing of presenilin 2 in a cell, isolated compounds that inhibit proteolytic processing of presenilin 2 in a cell, and a method of inhibiting apoptotic cell death by preventing proteolytic cleavage of presenilin 2 at a cleavage site which generates a 20 kDa C-terminal fragment.

6 Claims, 17 Drawing Sheets

OTHER PUBLICATIONS

Inoue, S., et al., "Inhibition of Degradation of 3–Hydroxy–3–methylglutaryl–coenzyme A Reductase in Vivo by Cysteine Protease Inhibitors," *J. Biol. Chem.* 266:13311–13317 (1991).

Jacobson, M.D., et al., "Programmed Cell Death in Animal Development," *Cell* 88:347–354 (Feb. 1997).

Jensen, T.J., et al., "Multiple Proteolytic Systems, including the Proteasome, Contribute to CFTR Processing," *Cell* 33:129–135 (1995).

Johnson, E.M., Jr., "Possible Role of Neuronal Apoptosis in Alzheimer's Disease," *Neurobiology of Aging* 15 (*Suppl.* 2):s187–s189 (1994).

Kim, T.–W., et al., "Proteolytic Processing and Ubiquitin–Dependent Degradation of Alzheimer–Associated Presenilin 1 and 2," *Soc. Neurosci. Abstr.* 22:727, Abstract No. 293.5 (Nov. 1996).

Kim, T.–W., et al., "Endoproteolytic Cleavage and Proteasomal Degradation of Presenilin 2 in Transfected Cells," *J Biol Chem* 272:11006–11010 (Apr. 1997).

Kim, T.–W., et al., "Alternative Cleavage of Alzheimer–Associated Presenilins During Apoptosis by a Caspase–3 Family Protease," *Science* 277:373–376 (Jul. 1997).

Koo, E.H., and Squazzo, S.L., "Evidence That Production and Release of Amyloid β–Protein Involves the Endocytic Pathway," *J. Biol. Chem.* 269:17386–17389 (1994).

Kovacs, D.M., et al., "Alzheimer–associated presenilins 1 and 2: Neuronal expression in brain and localization to intracellular membranes in mammalian cells," *Nature Medicine* 2:224–229 (Feb. 1996).

L'Hernault, S.W., and Arduengo, P.M., "Mutation of a Putative Sperm Membrane Protein in *Caenorhabditis elegans* Prevents Sperm Differentiation but Not Its Associated Meiotic Divisions," *J. Cell Biol.* 119:55–68 (1992).

LaFerla, F.M., et al., "The Alzheimer's Aβ peptide induces neurodegeneration and apoptotic cell death in transgenic mice," *Nature Genetics* 9:21–30 (1995).

LeBlanc, A., "Apoptosis and Alzheimer's Disease," in *Molecular Mechanisms of Dementia*, Wasco, W., and Tanzi, R.E., eds., Humana Press, Totowa, NJ, pp. 57–71 (Nov. 1996).

Lee, M.K., et al., "Expression of Presenilin 1 and 2 (PS1 and PS2) in Human and Murine Tissues," *J. Neurosci,* 16:7513–7525 (Dec. 1996).

Levitan, D., and Greenwald, I., "Facilitation of lin–12–mediated signalling by sel–12, a *Caenorhabditis elegans* S182 Alzheimer's disease gene," *Nature* 377:351–354 (1995).

Levy–Lahad, E., et al., "Candidate Gene for the Chromosome 1 Familial Alzheimer's Disease Locus," *Science* 269:973–977 (1995).

Li, X., and Greenwald, I., "Membrane Topology of the *C. elegans* SEL–12 Presenilin," *Neuron* 17:1015–1021 (Nov. 1996).

Martin, S.J., and Green, D.R., "Protease Activation during Apoptosis: Death by a Thousand Cuts?," *Cell* 82:349–352 (1995).

McGee, T.P., et al., "Degradation of 3–Hydroxy–3–methylglutaryl–CoA Reductase in Endoplasmic Reticulum Membranes Is Accelerated as a Result of Increased Susceptibility to Proteolysis," *J. Biol. Chem.* 271:25630–25638 (Oct. 1996).

Page, K., et al., "In situ hybridization analysis of presenilin 1 mRNA in Alzheimer disease and in lesioned rat brain," *Proc. Natl. Acad. Sci. USA* 93:14020–14024 (Nov. 1996).

Pai, J.–T., et al., "Purificaiton and cDNA cloning of a second apoptosis–related cysteine protease that cleaves and activates sterol regulatory element binding proteins," *Proc. Natl. Acad. Sci. USA* 93:5437–5442 (May 1996).

Paradis, E., et al., "Amyloid β Peptide of Alzheimer's Disease Downregulates Bcl–2 and Upregulates Bax Expression in Human Neurons," *J. Neurosci.* 16:7533–7539 (Dec. 1996).

Perez–Tur, J., et al., "A mutation in Alzheimer's disease destroying a splice acceptor site in the presenilin–1 gene," *NeuroReport* 7:297–301 (1995).

Rock, K.L., et al., "Inhibitors of the Proteasome Block the Degradation of Most Cell Proteins and the Generation of Peptides Presented on MHC Class I Molecules," *Cell* 78:761–771 (1994).

Rogaev, E.I., et al., "Familial Alzheimer's disease in kindreds with missense mutations in a gene on chromosome 1 related to the Alzheimer's disease type 3 gene," *Nature* 376:775–778 (1995).

Roitelman, J., et al., "Immunological Evidence for Eight Spans in the Membrane Domain of 3–Hydroxy–3–Methylglutaryl Coenzyme A Reductase: Implications for Enzyme Degradation in the Endoplasmic Reticulum," *J. Cell Biol.* 117:959–973 (1992).

Sakai, J., et al., "Sterol–Regulated Release of SREBP–2 from Cell Membranes Requires Two Sequential Cleavages, One Within a Transmembrane Segment," *Cell* 85:1037–1046 (Jun. 1996).

Schellenberg, G.D., "Genetic dissection of Alzheimer disease, a heterogeneous disorder," *Proc. Natl. Acad. Sci. USA* 82:8552–8559 (1995).

Scheuner, D., et al., "Secreted amyloid β–protein similar to that in the senile plaques of Alzheimer's disease is increased in vivo by the presenilin 1 and 2 and APP mutations linked to familial Alzheimer's disease," *Nature Medicine* 2:864–870 (Aug. 1996).

Sherrington, R., et al., "Cloning of a gene bearing missense mutations in early–onset familial Alzheimer's disease," *Nature* 375:754–760 (1995).

Sutcliffe, J.G., et al., "Antibodies That React with Predetermined Sites on Proteins," *Science* 219:660–666 (1983).

Tanzi, R.E., et al., "The Gene Defects Responsible for Familial Alzheimer's Disease," *Neurobiology of Disease* 3:159–168 (Nov. 1996).

Thinakaran, G., et al., "Endoproteolysis of Presenilin 1 and Accumulation of Processed Derivatives In Vivo," *Neuron* 17:181–190 (Jul. 1996).

Thompson, C.B., "Apoptosis in the Pathogenesis and Treatment of Disease," *Science* 267:1456–1462 (1995).

Tomita, T., et al., "The presenilin 2 mutation (N141I) linked to familial Alzheimer disease (Volga German families) increases the secretion of amyloid β protein ending at the 42nd (or 43rd) residue," *Proc. Natl. Acad. Sci. USA* 94:2025–2030 (Mar. 1997).*

Walter, J., et al., "The Alzheimer's Disease–Associated Presenilins Are Differentially Phosphorylated Proteins Located Predominantly within the Endoplasmic Reticulum," *Molecular Medicine* 2:673–691 (Nov. 1996).*

Wang, X., et al., "SREBP–1, a Membrane–Bound Transcription Factor Released by Sterol–Regulated Proteolysis," *Cell* 77:53–62 (1994).*

Wang, X., et al., "Cleavage of sterol regulatory element binding proteins (SREBPs) by CPP32 during apoptosis," *EMBO J. 15*:1012–1020 (Mar. 1996).

Ward, C.L., et al., "Degradation of CFTR by the Ubiquitin–Proteasome Pathway," *Cell 83*:121–127 (1995).

Wasco, W., and Tanzi, R.E., "Molecular genetics of amyloid and apolipoprotein E in Alzheimer's disease," in *Neurobiology of Alzheimer's Disease*, Dawbarn, D., and Allen, S.J., eds., Bios Scientific Publishers Limited, Oxford, UK, pp. 51–76 (1995).

Wiertz, E.J.H.J., et al., "Sec61–mediated transfer of a membrane protein from the endoplasmic reticulum to the proteasome for destruction," *Nature 384*:432–438 (Dec. 1996).

Wolozin, B., et al., "Participation of Presenilin 2 in Apoptosis: Enhanced Basal Activity Conferred by an Alzheimer Mutation," *Science 274*:1710–1713 (Dec. 1996).

Xia, W., et al., "Enhanced Production and Oligomerization of the 42–residue Amyloid β–Protein by Chinese Hamster Ovary Cells Stably Expressing Mutant Presenilins," *J. Biol. Chem. 272*:7977–7982 (Mar. 1997).

Yankner, B.A., et al., "Neurotrophic and Neurotoxic Effects of Amyloid β Protein: Reversal by Tachykinin Neuropeptides," *Science 250*:279–282 (1990).

* cited by examiner

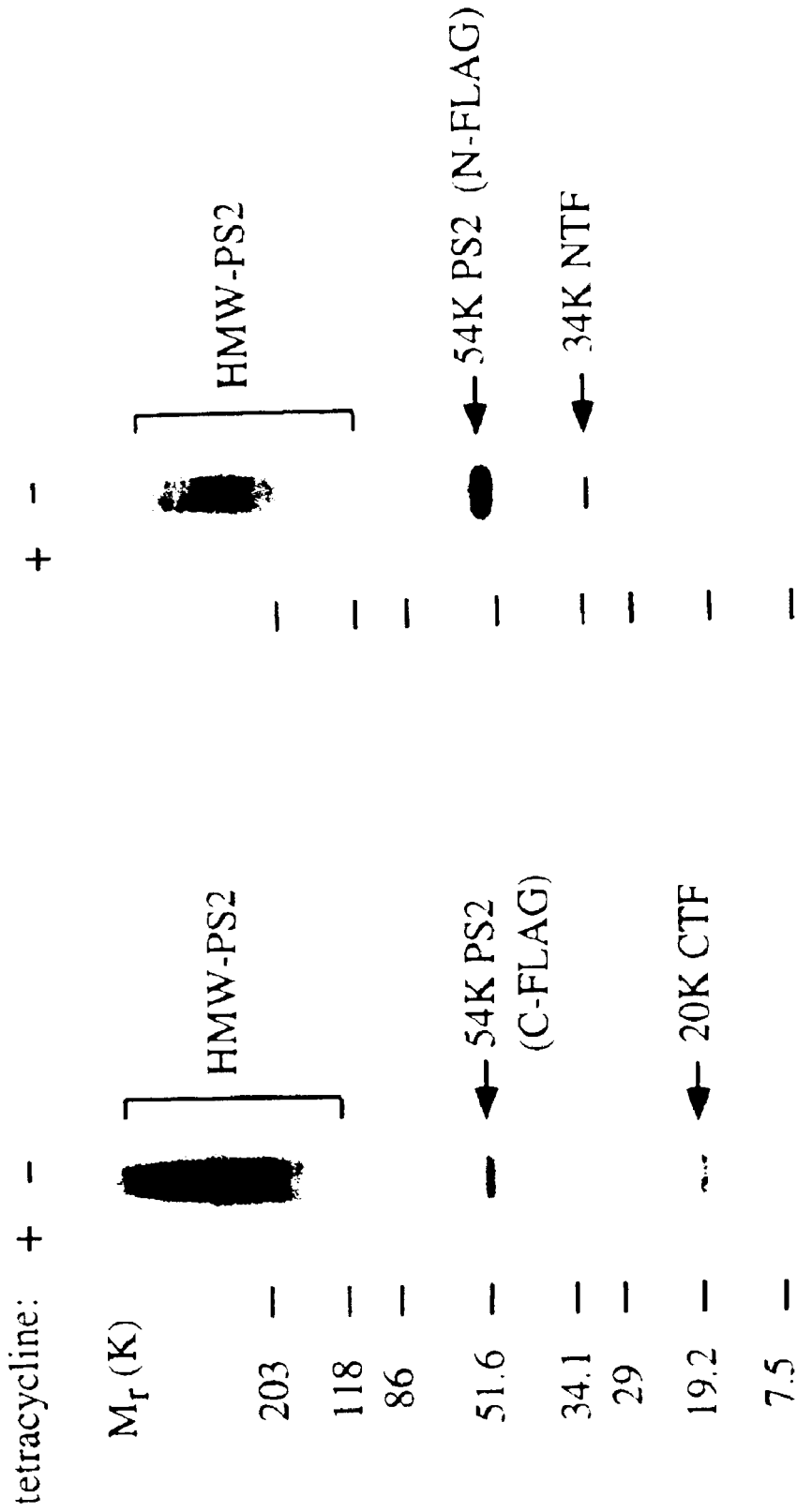

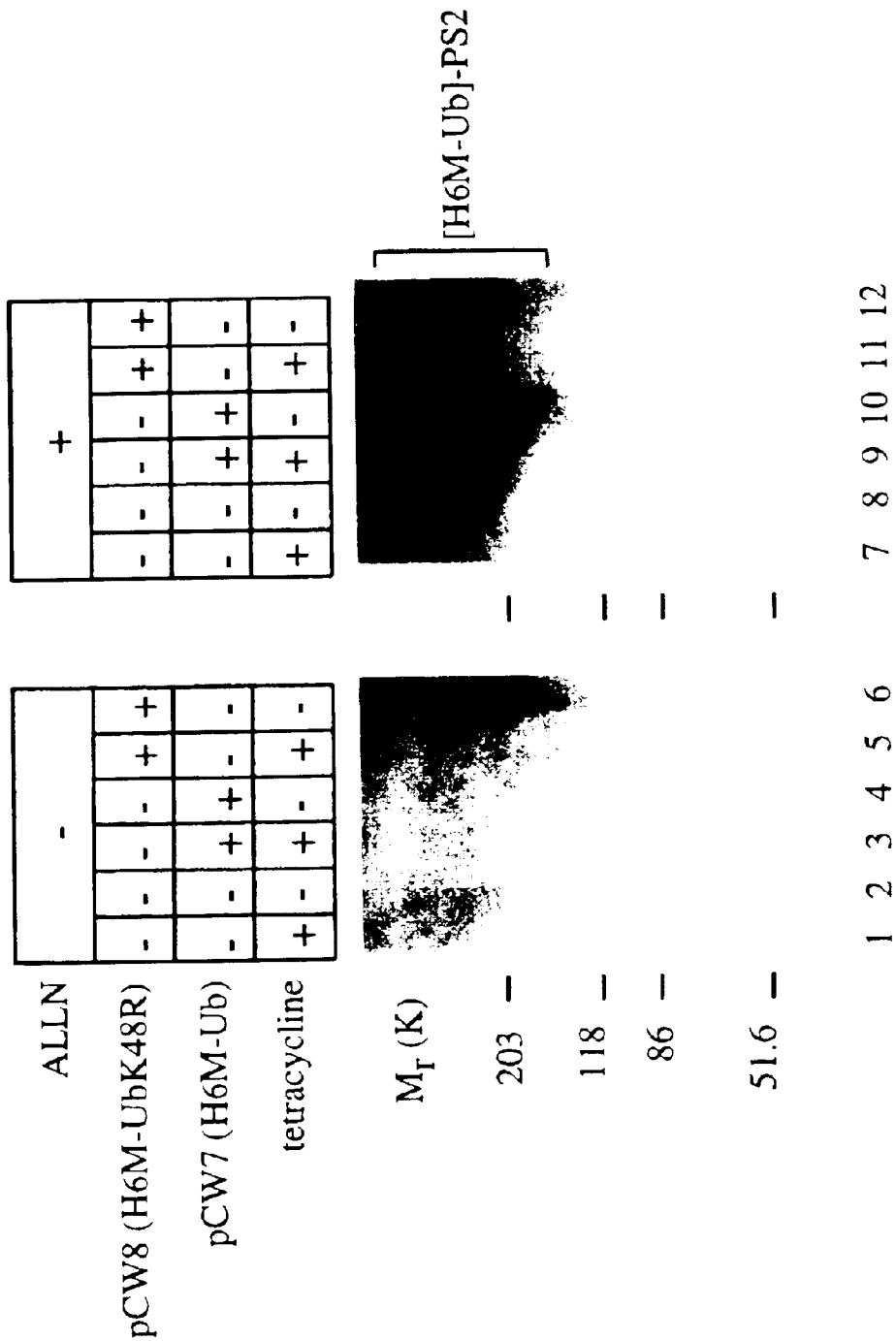

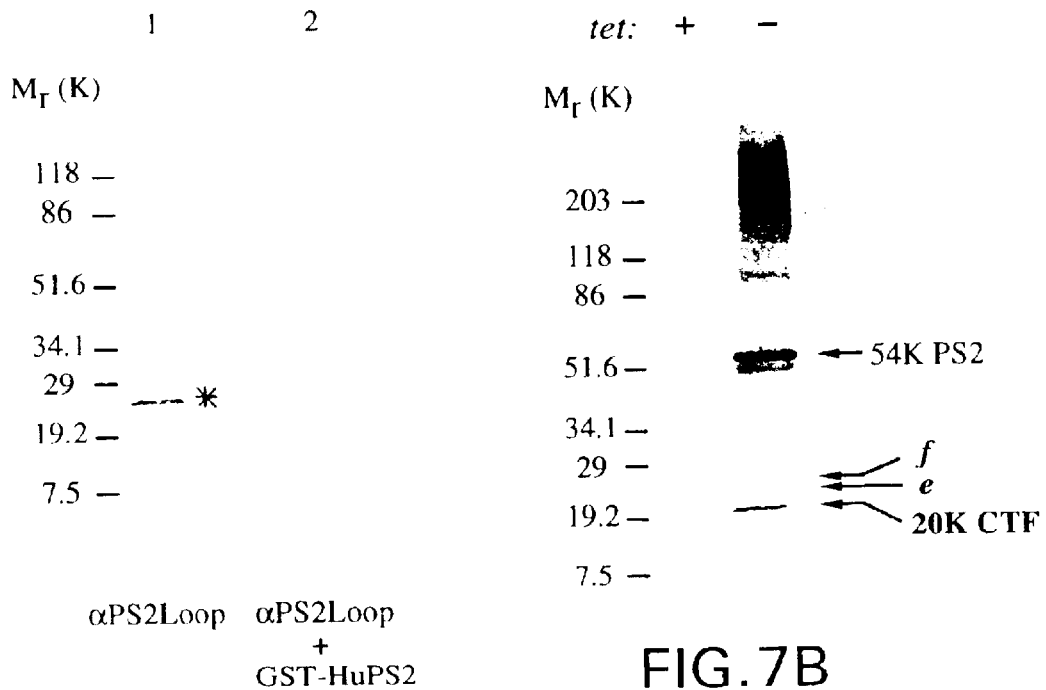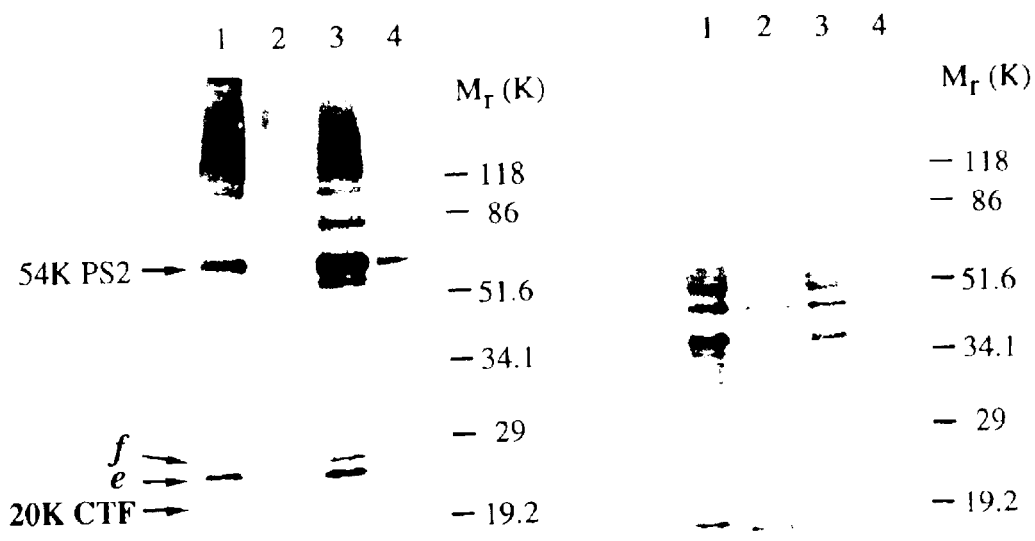

Uninduced

Induced

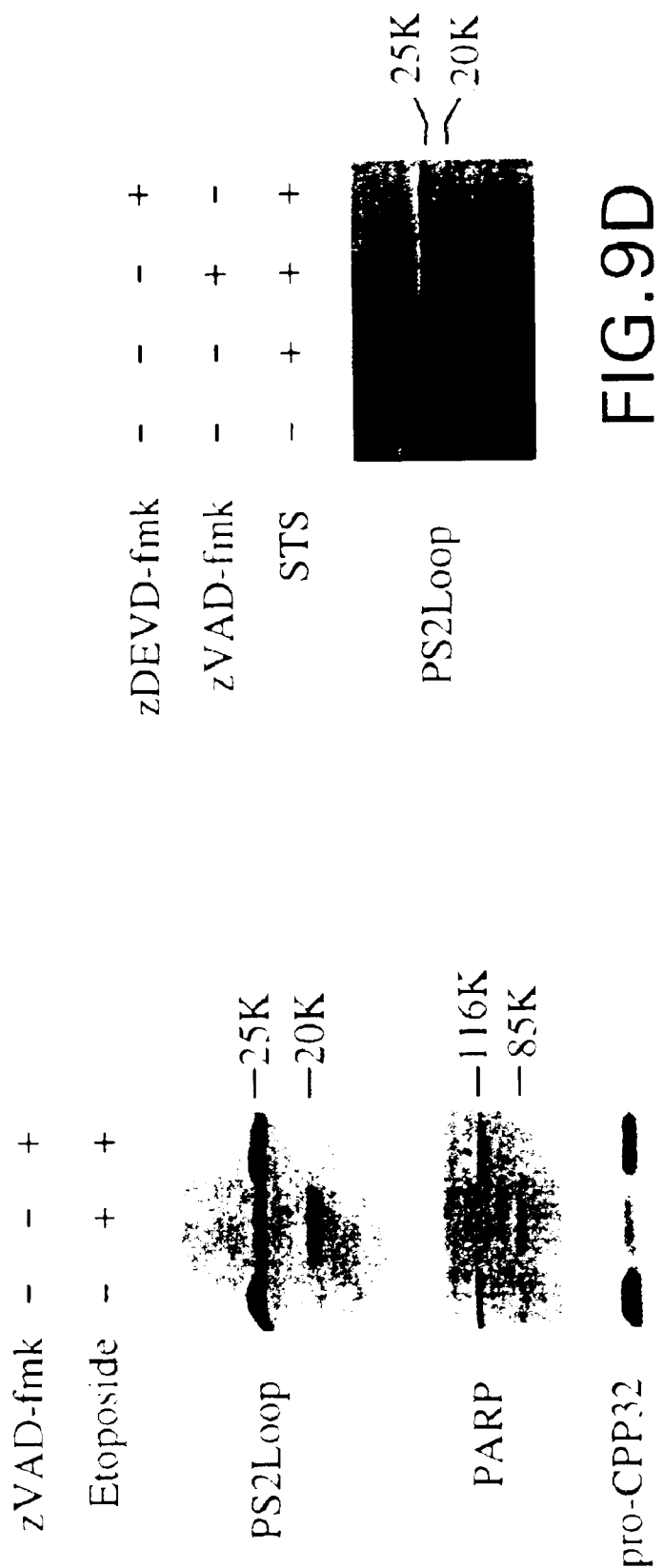

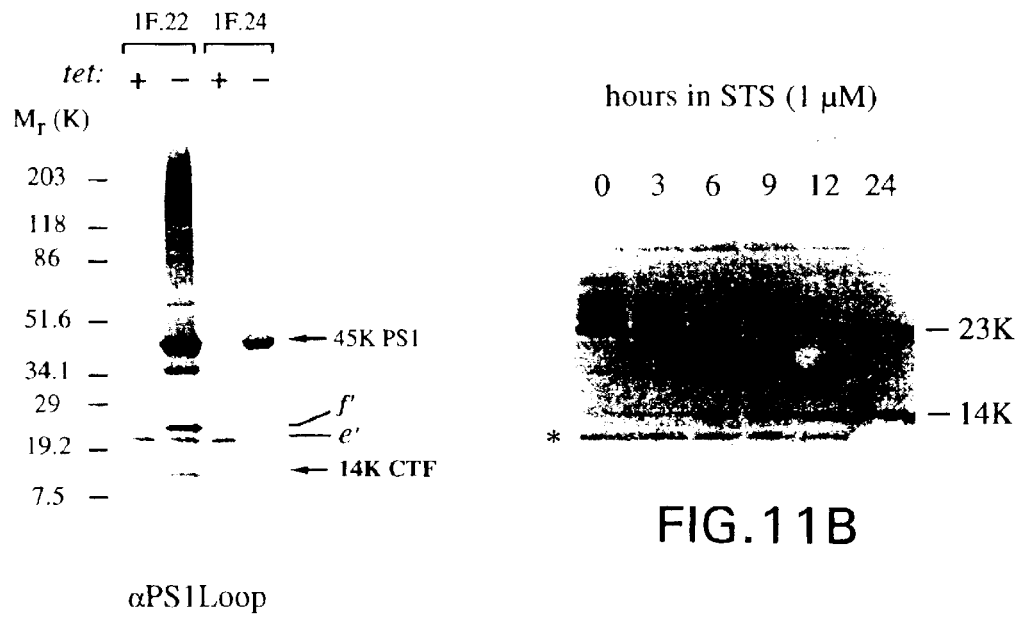
FIG.11A
FIG.11B
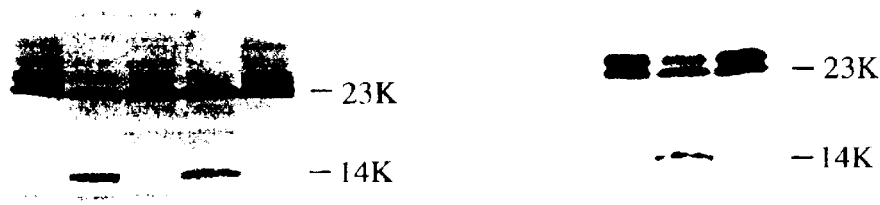
FIG.11C
FIG.11D

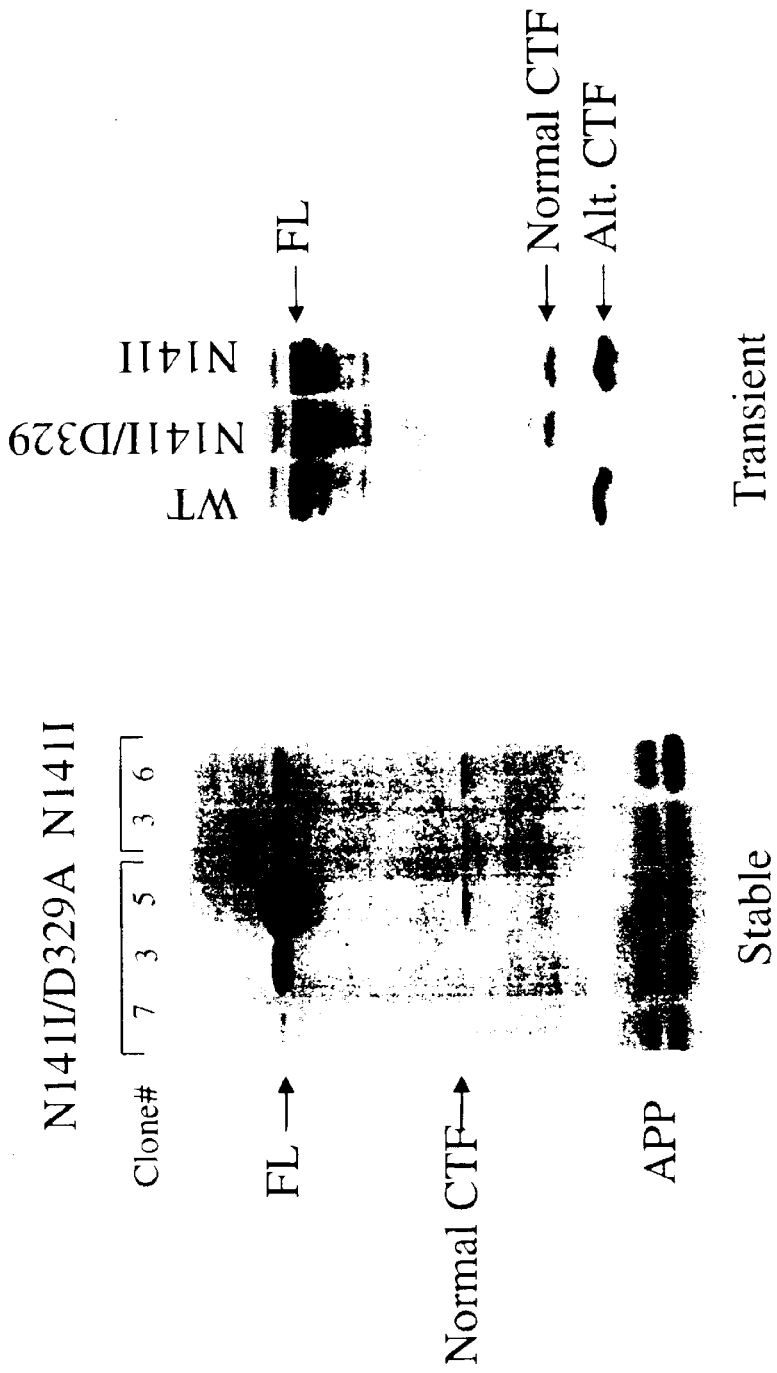

PURIFIED 20 KDA PRESENILIN 2 C-TERMINAL FRAGMENT AND METHODS OF SCREENING FOR COMPOUNDS THAT INHIBIT PROTEOLYSIS OF PRESENILIN 2

CROSS REFERENCES TO RELATED APPLICATIONS

This application is a Non-Provisional of U.S. Application Ser. No. 60/044,262, filed Apr. 24, 1997, which is relied upon and incorporated by reference herein in its entirety.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates, in general, to presenilin 2 proteolytic fragments. In particular, the present invention relates to a purified 20 kDa presenilin 2 C-terminal fragment (PS2-CTF); purified nucleic acid molecules coding for the 20 kDa PS2-CTF protein; cells containing the nucleic acid molecules; non-human organisms containing the nucleic acid molecule; antibodies having specific binding affinity to the 20 kDa PS2-CTF; hybridomas containing the antibodies; methods of detecting 20 kDa PS2-CTF in a sample; diagnostic kits; methods for screening compounds that inhibit proteolytic processing of presenilin 2 in a cell, isolated compounds that inhibit proteolytic processing of presenilin 2 in a cell, and methods of inhibiting apoptotic cell death by preventing proteolytic cleavage of presenilin 2 at a cleavage site which generates a 20 kDa C-terminal fragment.

2. Related Art

A significant portion of Alzheimer's disease (AD) is attributed to specific gene defects leading to familial Alzheimer's disease (FAD) (Wasco, W., and Tanzi, R. E., in *Molecular Genetics of Amyloid and Apolipoprotein E in Alzheimer's Disease* (Dawbard, D., and Allen, B. J., eds), BIOS Scientific, Oxford, UK, (1995), pp. 51–76; Schallenberg, G. D., *Proc. Natl. Acad. Sci. USA* 92:8552–8559 (1995); Tanzi, R. E., el al., *Neurobiol. Dis.* 3:159–168 (1996); Sherrington, R., et al., *Nature,* 375:754–760 (1995); Levy-Lahad, E., et al., *Science* 269:973–977 (1995)). Two homologous genes; presenilin 1 (PS1) and presenilin 2 (PS2), are responsible for at least 50% of early onset (<60 years old) FAD (Schallenberg, G. D., *Proc. Natl. Acad. Sci. USA* 92:8552–8559 (1995); Tanzi, R. E., et al., *Neurobiol. Dis.* 3:159–168 (1996)). PS1 and PS2 are serpentine proteins consisting of six to nine predicted transmembrane domains interspersed with one large and multiple smaller hydrophilic loops (Sherrington, R., et al., *Nature,* 375:754–760 (1995); Levy-Lahad, E., et al., *Science* 269:973–977 (1995)). At the amino acid level, the two proteins are 67% identical and exhibit significant homology to two *Caenorhabditis elegans* gene products, sel-12 (approximately 50% identity) which has been predicted to facilitate Notch receptor function (Levitan, D., and Greenwald, I., *Nature* 377:351–354 (1995)), and spe-4 (approximately 26% identity) which is involved in cytoplasmic trafficking of proteins during spermatogenesis (L'Hernault, S. W., and Arduengo, P. M., *J. Cell Biol.* 119:55–68 (1992)).

PS1 and PS2 are ubiquitously expressed (Sherrington, R., et al., *Nature,* 375:754–760 (1995); Levy-Lahad, E., et al., *Science* 269:973–977 (1995)) and in brain are expressed primarily in neurons, with similar regional distributions (Kovacs, D. M., et al., *Nat. Med.* 2:224–229 (1996); Lee, M. K., et al., *J. Neurosci.* 16:7513–7525 (1996); Page, K., et al., *Proc. Natl. Acad. Sci. USA* 93:14020–14024 (1996)). The presenilins are localized to the endoplasmic reticulum (ER) and the Golgi apparatus but not the plasma membrane suggesting a potential role in protein processing (Kovacs, D. M., et al., *Nat. Med.* 2:224–229 (1996); Cook, D. G., *Proc. Natl. Acad. Sci. USA* 93:9223–9228 (1996); Walter, J., et al., *Mol. Med.* 2:673–691 (1996)). To date, the PS1 and PS2 genes have been shown to contain 35 different mutations which are inherited in an autosomal dominant fashion in over 60 kindreds with early onset FAD (Sherrington, R., et al., *Nature,* 375:754–760 (1995); Levy-Lahad, E., el al., *Science* 269:973–977 (1995); Rogasv, L. L., et al., *Nature* 376:775–778 (1995); for summary, see Kovacs, D. M., et al., *Nat. Med.* 2:224–229 (1996)). Recent studies suggest that the presenilins may directly or indirectly affect the processing of amyloid P-protein precursor, APP, leading to increased production of AP42 (Scheuner, D., et al., *Nat. Med.* 2:864–870 (1995); Duff, K., et al., *Nature* 383:710–713 (1996); Borchalt, D. R., et al., *Neuron* 17:1005–1013 (1995); Citron, M., et al., *Nat. Med.* 3:67–72 (1996)). These results help to explain the relatively high degree of amyloid burden in the brains of FAD patients carrying PS1 and PS2 mutations. The pathogenic mechanism by which presenilin mutations lead to increased P-amyloid deposition and other neuropathological features of AD remains unclear. To understand the role(s) of PS2 in normal cellular metabolism and AD pathogenesis, the processing and degradation pathways of PS2 was investigated.

SUMMARY OF THE INVENTION

The invention provides, in general, purified presenilin 2 fragments.

The invention further provides a purified 20 kDa presenilin 2 C-terminal fragment (PS2-CTF).

The invention also provides an antibody having specific binding affinity to the 20 kDa PS2-CTF.

The invention further provides a method of detecting 20 kDa PS2-CTF in a sample, comprising:
  a) contacting the sample with the above-described antibody, under conditions such that immunocomplexes form, and
  b) detecting the presence of said antibody bound to the polypeptide.

The invention also provides a diagnostic kit comprising:
  a) a first container means containing the above-described antibody and
  b) a second container means containing a conjugate comprising a binding partner of the antibody and a label.

The invention further provides a hybridoma which produces the above-described antibody.

The invention also provides an isolated nucleic acid molecule encoding 20 kDa PS2-CTF.

The invention further provides a cell that contains the above-described nucleic acid molecule.

The invention also provides a non-human organism that contains the nucleic acid molecule.

The invention further provides a method for screening compounds that inhibit proteolytic processing of presenilin 2 in a cell comprising (a) providing a compound to a cell, wherein the cell proteolytically processes presenilin 2, (b) measuring the amount of 20 kDa presenilin 2 C-terminal fragment (PS2-CTF) produced in the cell, and (c) comparing the amount produced to an amount of PS2-CTF produced in a cell not treated with the compound, wherein a decreased amount of 20 kDa presenilin 2 fragment in the cell treated with the compound as compared to a cell not treated with the compound indicates that the compound inhibits proteolytic processing of presenilin 2 in the cell.

The invention also provides a method of inhibiting apoptotic cell death comprising preventing proteolytic cleavage of presenilin 2 at the cleavage site which generates the 20 kDa C-terminal proteolytic fragment.

Further objects and advantages of the present invention will be clear from the description that follows.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

Purified. A "purified" protein or nucleic acid is a protein or nucleic acid that has been separated from a cellular component. "Purified" proteins or nucleic acids have been purified to a level of purity not found in nature.

Substantially Pure. A "substantially pure" protein or nucleic acid is a protein or nucleic acid preparation that is lacking in all other cellular components.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Polyacrylamide Gel Electrophoresis (PAGE). The most commonly used technique (though not the only one) for achieving a fractionation of polypeptides on the basis of size is polyacrylamide gel electrophoresis. The principle of this method is that polypeptide molecules migrate through the gel as though it were a sieve that retards the movement of the largest molecules to the greatest extent and the movement of the smallest molecules to the least extent. Note that the smaller the polypeptide fragment, the greater the mobility under electrophoresis in the polyacrylamide gel. Both before and during electrophoresis, the polypeptides typically are continuously exposed to the detergent sodium dodecyl sulfate (SDS), under which conditions the polypeptides are denatured. Native gels are run in the absence of SDS. The polypeptides fractionated by polyacrylamide gel electrophoresis can be visualized directly by a staining procedure if the number of polypeptide components is small.

Western Transfer Procedure. The purpose of the Western transfer procedure (also referred to as blotting) is to physically transfer polypeptides fractionated by polyacrylamide gel electrophoresis onto a nitrocellulose filter paper or another appropriate surface or method, while retaining the relative positions of polypeptides resulting from the fractionation procedure. The blot is then probed with an antibody that specifically binds to the polypeptide of interest.

Isolated Nucleic Acid Molecule. An "isolated nucleic acid molecule", as is generally understood and used herein, refers to a polymer of nucleotides, and includes but should not be limited to DNA and RNA. The "isolated" nucleic acid molecule is purified from its natural in vivo state.

Recombinant DNA. Any DNA molecule formed by joining DNA segments from different sources and produced using recombinant DNA technology (aka. molecular genetic engineering).

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

BRIEF DESCRIPTION OF THE FIGURES

FIG. 1A) or in N terminus (clone: 5WF11; FIG. 1B). Full-length PS2 with an apparent molecular mass of 53–55 kDa (54K PS2) and a high molecular mass form of PS2 (HMW-PS2) were detected in Western blot analysis using monoclonal anti-FLAG antibody, M2. In addition, 20-kDa C-terminal (PS2-CTF: FIG. 1A) and 34-kDa-terminal (PS2-NTF: FIG. 1B) fragments were also detected only in the induced (-tetracycline) lanes.

FIG. 5. Polyubiquitination and proteasomal degradation of PS2.

FIG. 7. Aberrant 20 kDa PS2 C-terminal fragment (CTF) in transfected cells. (a) Detection of the endogenous PS2 CTF in human brain. The αPS2Loop detected 25 kDa protein (indicated by asterisk) but not full-length PS2 in the total homogenate (80 µg protein) prepared from human temporal cortex (lane 1). The immunoreactivity was abolished by preabsorption with the antigen polypeptide-GST-HuPS2 (lane 2). (b) Detection of multiple PS2 CTFs in the inducible H4 cells overexpressing C-terminal epitope-tagged PS2 by Western blotting using αPS2Loop. The 25 kDa endogenous PS2 fragment (designated by arrow e) was detected in both uninduced (tet+) and induced (tet−) samples. Two additional fragments, including 26 kDa fragment representing normal cleavage product (designated by the arrow f), and the smaller 20 kDa fragment (20K CFT), were detected only in the induced (tet−) samples. (c) Selective localization of the 20 kDa CTF in the non-ionic detergent-resistant cellular fraction. Wild-type PS2 cells were induced for 48 hours, fractionated into detergent-insoluble/resistant (lane 2) and detergent soluble (lane 3) fractions and wash (lane 4), and then analyzed by Western blotting with αPS2Loop. Total SDS lysates are shown in lane 1. (d) Generation of 20 kDa PS2 CTF was blocked by zVAD-fmk (a broad spectrum capsase inhibitor) and zDEVD-fmk (CPP32-like protease inhibitor) in cells overexpressing PS2. The zFA-fmk (cathepsin B inhibitor) was used as a control for fluoromethylketone (fmk) group. Inhibitors were purchased from Enzyme Systems Products (Dublin, Calif.). Inducible PS2 were grown in the presence (Uninduced, left panel) or absence (Induced, right panel) of tetracycline for 24 hours, and inhibitors or solvent (DMSO) were added at the time of the induction.

FIG. 11. (a) Detection of alternatively cleaved 14 kDa PS1 CTF in H4 cells overexpressing C-terminal epitope-tagged PS 1. Inducible PS1 cells were generated similar to as described herein. High-(clone 1.22) and low-(clone 1.24) expressing clones were grown in the presence or absence of tetracycline for 24 hours. As similar to those shown for PS2, multiple PS1 CTFs were detected in the PS 1-overproducing cells, including 23 kDa endogenous PS1 CTF (arrow e'), transgene-derived normal cleavage product (arrow f'), and aberrant 14 kDa PS1 fragment. (b, c, d) Cleavage of endogenous PS1 CTF during STS-induced apoptosis. Identical samples used for FIG. 8 were stained with αPS1 Loop. PS1 CTF was further cleaved into smaller 14 kDa fragment during apoptotic process. Inhibition of STS-induced (c) and etoposide-induced (d) PS1 cleavage by zVAD-fmk. Asterisk indicates non-specific bands.

FIG. 13. Western blot analysis of cellular lysates prepared from representative, stably transfected clonal cell lines. Establishment of stable CHO cell lines co-expressing APP and PS2 containing N141I (Volga German) and D329A (Caspase Clip site) mutations. Panel (a) Stable CHO cells expressing PS2 with N141I/D329A (clone # 3, 5, and 7) or N141I (clone # 3, and 6), full-length PS2 (FL) with apparent molecular weight 53 kDa and normal C-terminal fragment (CTF). Panel (b) Generation of alternative CTF was abolished in the CHO cells transfected with PS2 containing N 141 I/D329A mutations.

DETAILED DESCRIPTION OF THE PREFERRED EMBODIMENTS

Figure 2A:
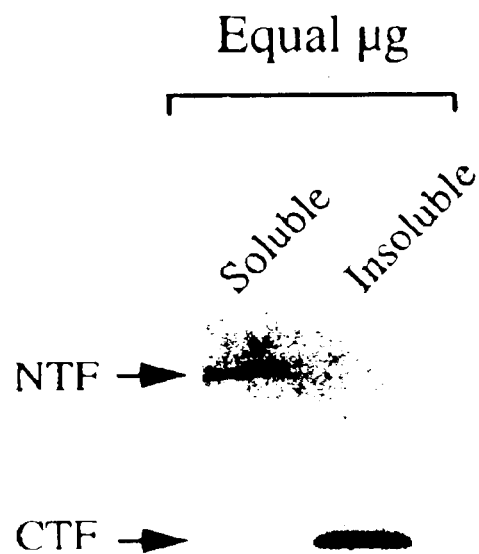
FIG. 2. Detergent solubility of C- and N-terminal PS2 fragments. Cells expressing either C-terminal or N-terminal epitope-tagged PS2 were induced for 48 h, extracted as described herein. Equal amounts of proteins (FIG. 2A) were analyzed by Western blotting using anti-FLAG antibody, and equal volumes (FIG. 2B) were normalized for total cellular proteins using the αPS2Loop. While 34-kDa-terminal fragments (NTF) were only detectable in detergent-extractable cellular pools, the 20-kDa C-terminal fragment (CTF) was highly concentrated in the detergent-resistant cellular fraction.

For purposes of clarity of disclosure, and not by way of limitation, the detailed description of the invention is divided into the following subsections:

I. Purified Presenilin 2 Proteolytic Fragments.
II. An Antibody Having Binding Affinity to a Presenilin 2 Proteolytic Fragment and a Hybridoma Containing the Antibody.
III. A Method of Detecting a Presenilin 2 Proteolytic Fragment or Antibody in a Sample.
IV. A Diagnostic Kit Comprising a Presenilin 2 Proteolytic Fragment or Antibody.
V. Isolated Nucleic Acid Molecules Coding for a Presenilin 2 Proteolytic Fragment.
VI. DNA Constructs Comprising a Nucleic Acid Molecule Encoding a Presenilin 2 Proteolytic Fragment and Cells Containing These Constructs.
VII. Methods of Screening for Compounds that Inhibit Proteolysis of Presenilin 2
VIII. Diagnostic Screening I. Purified Presenilin 2 Proteolytic Fragments Mutations in the presenilin genes, PS1 and PS2, cause a major portion of early onset familial Alzheimer's disease (FAD). The biological roles of the presenilins and how their pathological mutations confer FAD are unknown. The processing and degradation pathways of PS2 are described herein. For regulated expression of PS2, inducible cell lines expressing PS2 under the tight control of the tetracycline-responsive transactivator were established. Western blot analysis revealed that PS2 was detected as an ~53–55-kDa polypeptide (54-kDa PS2) as well as a high molecular mass form (HMW-PS2). Using a stably transfected, inducible cell system, it was found that PS2 is proteolytically cleaved into two stable cellular polypeptides including an ~20-kDa C-terminal fragment and an ~34-kDa N-terminal fragment. PS2 is polyubiquitinated in vivo, and the degradation of PS2 is inhibited by proteasome inhibitors, N-acetyl-L-leucinal-L-norleucinal and lactacystin. These studies suggest that PS2 normally undergoes endoproteolytic cleavage and is degraded via the proteasome pathway.

Both PS1 and PS2 were alternatively cleaved at sites distal to their normal cleavage sites when apoptosis was induced in untransfected H4 human neuroglioma cells, or when these genes were overexpressed. Alternative cleavage of PS1 and PS2 could be blocked by treatment with either zVAD (a broad spectrum caspase inhibitor) or zDEVD (CPP32-like protease inhibitor), indicating that the enzyme responsible is a CPP32-like protease. In PS2, this alternative cleavage site was identified as DSYDS (a.a. 326–330)(SEQ ID NO: 1). In H4 cells overexpressing PS2 containing the N141I FAD mutation, the ratio of apoptotic:normal cleavage fragments was significantly elevated compared to wild-type PS2-expressing cells. Thus, apoptosis-associated endoproteolysis of the presenilins mediated by a CPP32-like protease plays a role in the pathogenesis of FAD.

In one embodiment, the present invention relates to a purified polypeptide (preferably, substantially pure) having an amino acid sequence corresponding to a presenilin 2 proteolytic fragment, or a functional derivative thereof. In a preferred embodiment, the fragment is the about 26 kDa presenilin 2 C-terminal fragment (PS2-CTF), the fragment is the about 25 kDa presenilin 2 C-terminal fragment (PS2-CTF), the fragment is the about 20 kDa presenilin 2 C-terminal fragment (PS2-CTF), or the about 34 kDa presenilin 2 N-terminal fragment (PS2-NTF). The presenilin 2 gene was described by Levy-Lahad et al., *Science* 269: 973–977 (1995). The about 20 kDa presenilin 2 C-terminal fragment (PS2-CTF) preferably has an N-terminus of PEMEED (SEQ ID NO: 2) or PEMEEDSYD (SEQ ID NO: 3).

In a preferred embodiment, the invention relates to presenilin 2 proteolytic fragment epitopes. The epitope of these fragments is an immunogenic or antigenic epitope. An immunogenic epitope is that part of the entire fragment which elicits an antibody response when the whole fragment is the immunogen. An antigenic epitope is a fragment of the presenilin 2 proteolytic fragment which can elicit an antibody response. Methods of selecting antigenic epitope fragments are well known in the art. See, Sutcliffe et al., *Science* 219:660–666 (1983). Antigenic epitope-bearing peptides and polypeptides of the invention are useful to raise an immune response that specifically recognizes the polypeptides.

Amino acid sequence variants of presenilin 2 proteolytic fragments can be prepared by mutations in the DNA. Such variants include, for example, deletions from, or insertions or substitutions of, residues within the presenilin 2 proteolytic fragment amino acid sequence. Any combination of deletion, insertion, and substitution can also be made to arrive at the final construct, provided that the final construct possesses the desired activity.

While the site for introducing an amino acid sequence variation is predetermined, the mutation per se need not be predetermined. For example, to optimize the performance of a mutation at a given site, random mutagenesis can be conducted at the target codon or region and the expressed presenilin 2 proteolytic fragment variants screened for the optimal combination of desired activity. Techniques for making substitution mutations at predetermined sites in DNA having a known sequence are well known, for example, site-specific mutagenesis.

Preparation of a presenilin 2 proteolytic fragment variant in accordance herewith is preferably achieved by site-specific mutagenesis of DNA that encodes an earlier prepared variant or a nonvariant version of the protein. Site-specific mutagenesis allows the production of presenilin 2 proteolytic fragment variants through the use of specific oligonucleotide sequences that encode the DNA sequence of the desired mutation. In general, the technique of site-specific mutagenesis is well known in the art, as exemplified by publications such as Adelman et al., *DNA* 2:183 (1983) and Ausubel et al. "Current Protocols in Molecular Biology", J. Wiley & Sons, NY, N.Y., 1996.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete presenilin 2 proteolytic fragment sequence) can range generally from about 1 to 10 residues, more preferably 1 to 5.

The third group of variants are those in which at least one amino acid residue in the presenilin 2 proteolytic fragment molecule, and preferably, only one, has been removed and a different residue inserted in its place. Such substitutions preferably are made in accordance with the following Table 1 when it is desired to modulate finely the characteristics of the presenilin 2 proteolytic fragment.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of the presenilin 2 proteolytic fragment. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native presenilin 2 proteolytic fragment encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified presenilin 2 proteolytic fragment molecule variant is then screened in a suitable screening assay for the desired characteristic. For example, a change in the immunological character of the presenilin 2 proteolytic fragment molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the isolated nucleic acid fragments described herein can be used to express the presenilin 2 proteolytic fragment protein in any organism. The samples of the present invention include cells, protein extracts or membrane extracts of cells, or biological fluids. The sample will vary based on the assay format, the detection method and the nature of the tissues, cells or extracts used as the sample.

Any organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the presenilin 2 proteolytic fragment free of natural contaminants. These include, but are not limited to: immunochromotography, size-exclusion chromatography, HPLC, ion-exchange chromatography, and immuno-affinity chromatography.

In a preferred embodiment, the purification procedures comprise ion-exchange chromatography and size exclusion chromatography. Any one of a large number of ion-exchange resins known in the art can be employed, including for example, monoQ, sepharose Q, macro-prepQ, AG1-X2, or HQ. Examples of suitable size exclusion resins include, but are not limited to, Superdex 200, Superose 12, and Sephycryl 200. Elution can be achieved with aqueous solutions of potassium chloride or sodium chloride at concentrations ranging from 0.01 M to 2.0M.

II. An Antibody Having Binding Affinity to a Presenilin 2 Proteolytic Fragment and a Hybridoma Containing the Antibody.

In another embodiment, the present invention relates to an antibody having binding affinity specifically to a presenilin 2 proteolytic fragment as described above or specifically to a binding fragment of a presenilin 2 proteolytic fragment. Preferably, an antibody binds specifically to a presenilin 2 proteolytic 25 fragment or binding fragment thereof if it does not bind to presenilin 2. Preferably, the antibody would bind to the about 20 kDa presenilin 2 C-terminal fragment (PS2-CTF) and not to the about 34 kDa presenilin 2 N-terminal fragment (PS2-NTF). Alternatively, the antibody would bind to the about 34 kDa presenilin 2 N-terminal fragment (PS2-NTF) and not to the about 20 kDa presenilin 2 C-terminal fragment (PS2-CTF). Those which bind selectively to presenilin 2 proteolytic fragments would be chosen for use in methods which could include, but should not be limited to, the analysis of proteolytic cleavage of presenilin 2 in tissue containing presenilin 2.

The presenilin 2 proteolytic fragments of the present invention can be used in a variety of procedures and methods, such as for the generation of antibodies, and for use in identifying pharmaceutical compositions.

The presenilin 2 proteolytic fragments of the present invention can be used to produce antibodies or hybridomas. One skilled in the art will recognize that if an antibody is desired, such a fragment would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to presenilin 2 proteolytic fragments which are produced in humans, or are "humanized" (i.e. non-immunogenic in a human) by recombinant or other technology. Humanized antibodies can be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al, European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041–1043 (1988); Liu, A. Y. et al., Proc. Natl. Acad. Sci. USA 84:3439–3443 (1987); Liu, A. Y. et al., J. Immunol. 139:3521–3526 (1987); Sun, L. K. et al., Proc. Natl. Acad. Sci. USA 84:214–218 (1987); Nishimura, Y. et al, Canc. Res. 47:999–1005 (1987); Wood, C. R. et al., Nature 314:446–449 (1985)); Shaw et al., J. Natl. Cancer Inst. 80:1553–1559 (1988). General reviews of "humanized" chimeric antibodies are provided by Morrison, S. L. (Science, 229:1202–1207 (1985)) and by Oi, V. T. et al., BioTechniques 4:214 (1986)). Suitable "humanized" antibodies can be alternatively produced by CDR or CEA substitution (Jones, P. T. et al., Nature 321:552–525 (1986); Verhoeyan et al., Science 239:1534 (1988); Beidler, C. B. et al., J. Immunol. 141:4053–4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The presenilin 2 proteolytic fragment can be modified or administered in an adjuvant in order to increase the peptide antigenicity. Methods of increasing the antigenicity of a polypeptide are well known in the art. Such procedures include coupling the antigen with a heterologous protein (such as globulin or galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, NY, pp. 289–307 (1992), and Kaspczak et al., *Biochemistry* 28:9230–8 (1989).

III. A Method of Detecting a Presenilin 2 Proteolytic Fragment or Antibody in a Sample.

In another embodiment, the present invention relates to a method of detecting a presenilin 2 proteolytic fragment in a sample, comprising: a) contacting the sample with an above-described antibody (or protein), under conditions such that immunocomplexes form, and b) detecting the presence of the antibody bound to the fragment. In detail, the methods comprise incubating a test sample with one or more of the antibodies of the present invention and assaying whether the antibody binds to the test sample. Altered levels of presenilin 2 proteolytic fragments in a sample as compared to normal levels can indicate a specific disease (ex. familial Alzheimer's Disease (FAD)).

In a further embodiment, the present invention relates to a method of detecting a presenilin 2 proteolytic fragment antibody in a sample, comprising: a) contacting the sample with an above-described presenilin 2 proteolytic fragment, under conditions such that immunocomplexes form, and b) detecting the presence of the fragment bound to the antibody or antibody bound to the fragment. In detail, the methods comprise incubating a test sample with one or more of the fragments of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IV. A Diagnostic Kit Comprising a Presenilin 2 Proteolytic Fragment or Antibody.

In another embodiment of the present invention, a kit is provided which contains all the necessary reagents to carry out the previously described methods of detection.

The kit can comprise: i) a first container means containing an above-described antibody, and ii) second container means containing a conjugate comprising a binding partner of the antibody and a label.

The kit can comprise: i) a first container means containing an above-described fragment, and preferably, ii) second container means containing a conjugate comprising a binding partner of the fragment and a label. More specifically, a diagnostic kit comprises one or more presenilin 2 proteolytic fragments as described above, to detect antibodies in the serum of potentially infected animals or humans.

In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

V. Isolated Nucleic Acid Molecules Coding for a Presenilin 2 Proteolytic Fragment.

In one embodiment, the present invention relates to isolated (purified) presenilin 2 proteolytic fragment nucleic acid molecules. Preferably, the presenilin 2 proteolytic fragment nucleic acid molecule comprises a polynucleotide sequence at least 90% identical (more preferably, 95%, 96%, 97%, 98%, 99% or 100% identical) to the nucleic acid fragment encoding the about 26 kDa presenilin 2 C-terminal fragment (PS2-CTF), the about 25 kDa presenilin 2 C-terminal fragment (PS2-CTF), the about 20 kDa presenilin 2 C-terminal fragment (PS2-CTF), or the about 34 kDa presenilin 2 N-terminal fragment (PS2-NTF). The presenilin 2 gene was described by Levy-Lahad el al., Science 269: 973–977 (1995). The about 20 kDa presenilin 2 C-terminal fragment (PS2-CTF) preferably has an N-terminus of PEMEED (SEQ ID NO: 2) or PEMEEDSYD (SEQ ID NO: 3).

Also included within the scope of this invention are the functional equivalents of the herein-described isolated nucleic acid molecules and derivatives thereof. For example, the nucleic acid sequences described-above can be altered by substitutions, additions or deletions that provide for functionally equivalent molecules. Due to the degeneracy of nucleotide coding sequences, other DNA sequences which encode substantially the same amino acid sequence can be used in the practice of the present invention. These include but are not limited to nucleotide sequences comprising all or portions of nucleic acid encoding presenilin 2 proteolytic fragments which are altered by the substitution of different codons that encode a functionally equivalent amino acid residue within the sequence.

Further, it is possible to delete codons or to substitute one or more codons by codons other than degenerate codons to produce a structurally modified presenilin 2 proteolytic fragment, but one which has substantially the same utility or activity of the presenilin 2 proteolytic fragment produced by the unmodified nucleic acid molecule. As recognized in the art, the two fragments are functionally equivalent, as are the two nucleic acid molecules which give rise to their production, even though the differences between the nucleic acid molecules are not related to degeneracy of the genetic code.

VI. DNA Constructs Comprising a Nucleic Acid Molecule Encoding a Presenilin 2 Proteolytic Fragment and Cells Containing These Constructs.

In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

Two DNA sequences (such as a promoter region sequence and a presenilin 2 proteolytic fragment coding sequence) are said to be operably linked if the nature of the linkage between the two DNA sequences does not (1) result in the introduction of a frame-shift mutation, (2) interfere with the ability of the promoter region sequence to direct the transcription of the presenilin 2 proteolytic fragment coding sequence, or (3) interfere with the ability of the presenilin 2 proteolytic fragment coding sequence to be transcribed by the promoter region sequence. Thus, a promoter region would be operably linked to a DNA sequence if the promoter were capable of effecting transcription of that DNA sequence.

The present invention encompasses the expression of the presenilin 2 proteolytic fragment coding sequence (or a functional derivative thereof) in either prokaryotic or eukaryotic cells. Prokaryotic hosts are, generally, the most efficient and convenient for the production of recombinant proteins and, therefore, are preferred for the expression of the presenilin 2 proteolytic fragment coding sequence.

Prokaryotes most frequently are represented by various strains of E. coli. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC18, pUC19, pUC118, pUC119 and the like; suitable phage or bacteriophage vectors include λgt10, λgt11 and the like; and suitable virus vectors include pMAM-neo, pKRC and the like. Preferably, the selected vector of the present invention has the capacity to replicate in the selected host cell.

Recognized prokaryotic hosts include bacteria such as E. coli, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express a presenilin 2 proteolytic fragment in a prokaryotic cell, it is necessary to operably link the presenilin 2 proteolytic fragment coding sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of Bacillus (Gryczan, In: *The Molecular Biology of the Bacilli*, Academic Press, Inc., NY (1982)), and Streptomyces promoters (Ward et al., *Mol. Gen. Genet.* 203:468–478 (1986)). Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell.

Host cells which can be used in the expression systems of the present invention are not strictly limited, provided that they are suitable for use in the expression of the presenilin 2 proteolytic fragment of interest. Suitable hosts include eukaryotic cells.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the Drosophila alcohol dehydrogenase promoter can be used, Rubin, *Science* 240:1453–1459 (1988). Alternatively, baculovirus vectors can be engineered to express large amounts of presenilin 2 proteolytic fragment in insect cells (Jasny, *Science* 238:1653 (1987); Miller et al., In: *Genetic Engineering* (1986), Setlow, J. K., et al., eds., *Plenum*, Vol. 8, pp. 277–297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed.

Any of a series of yeast gene sequence expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of presenilin 2 proteolytic fragments.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of the presenilin 2 proteolytic fragment in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., Nature (London) 290:304–310 (1981)); the yeast gal4 gene sequence promoter (Johnston et al., *Proc. Natl. Acad. Sci. (USA)* 79:6971–6975 (1982); Silver et al., *Proc. Natl. Acad. Sci. (USA)* 81:5951–5955 (1984)) and the CMV immediate-early gene promoter (Thomsen el al., *Proc. Natl. Acad. Sci (USA)* 81:659–663 (1984).

As is widely known, translation of eukaryotic mRNA is initiated at the codon which encodes the first methionine. For this reason, it is preferable to ensure that the linkage between a eukaryotic promoter and a presenilin 2 proteolytic fragment coding sequence does not contain any intervening codons which are capable of encoding a methionine (i.e., AUG). The presence of such codons results either in a formation of a fusion protein or a frame-shift mutation (if the AUG codon is not in the same reading frame as the presenilin 2 proteolytic fragment coding sequence).

A presenilin 2 proteolytic fragment nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancer signal sequences, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in E. coli (such as, for example, pBR322, ColE1, pSC101, pACYC 184, π VX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)).

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the molecule results in the production of the presenilin 2 proteolytic fragment. This can take place in the transformed cells as such, or following the induction of these cells to differentiate (for example, by administration of bromodeoxyuracil to neuroblastoma cells or the like).

VII. Methods of Screening for Compounds that Inhibit Proteolysis of Presenilin 2

In another embodiment, the present invention relates to a method for screening compounds that inhibit proteolytic processing of presenilin 2 in a cell comprising (a) providing a compound to a cell, wherein the cell proteolytically processes presenilin 2, (b) measuring the amount of 20 kDa presenilin 2 C-terminal fragment (PS2-CTF) produced in the cell, and (c) comparing the amount produced to an amount of PS2-CTF produced in a cell not treated with the compound, wherein a decreased amount of 20 kDa presenilin 2 C-terminal fragment in the cell treated with the compound as compared to a cell not treated with the compound indicates that the compound inhibits proteolytic processing of presenilin 2 in the cell. Preferably, only proteolytic cleavage which results in the generation of the 20 kDa presenilin 2 C-terminal fragment is inhibited. In one prefered embodiment, inhibition of proteolytic cleavage at the 20 kDa presenilin 2 C-terminal fragment cleavage site comprises binding or the interaction of a compound at the 20 kDa presenilin 2 C-terminal fragment cleavage site.

In one prefered embodiment, the amount of 20 kDa presenilin 2 C-terminal fragment produced in the cell is determined by an ELISA assay using an antibody specific to the 20 kDa presenilin 2 C-terminal fragment.

In a further embodiment, the present invention relates to a method of inhibiting apoptotic cell death comprising preventing proteolytic cleavage of presenilin 2 at the cleavage site which generates the 20 kDa presenilin 2 C-terminal fragment. Preferably, the cleavage site is one of those set forth in FIG. 10A. In one prefered embodiment, only proteolytic cleavage which results in the generation of the 20 kDa presenilin 2 C-terminal fragment is inhibited (ie. proteolytic cleavage resulting in the 26 or 25 kDa C-terminal fragment is maintained).

Compounds which would inhibit proteolytic processing of presenilin 2 into the 20 kDa C-terminal fragment (and thus inhibit apoptotic cell death) include those which bind to or interact with the 20 kDa C-terminal proteolytic cleavage site. Accordingly, compounds which bind to the 20 kDa proteolytic site are included within the scope of the invention. In one prefered embodiment, the compounds bind to or interfer with the presenilin 2 amino acid sequence selected from the group consisting of PEMEED (SEQ ID NO: 2), PEMEEDS (SEQ ID NO: 4), PEMEEDSY (SEQ ID NO: 5), PEMEEDSYD (SEQ ID NO: 3), EMEEDS (SEQ ID NO: 6), EMEEDSY (SEQ ID NO: 7), EMEEDSYD (SEQ ID NO: 8), EEDSYD (SEQ ID NO: 9), EEDSYDS (SEQ ID NO: 10), EEDSYDSF (SEQ ID NO: 11), EDSYDS SEQ ID NO: 12), EDSYDSF (SEQ ID NO: 13), and EDSYDSFG (SEQ ID NO: 14).

VIII. Diagnostic Screening

It is to be understood that although the following discussion is specifically directed to human patients, the teachings are also applicable to any animal that expresses presenilin 2.

The diagnostic and screening methods of the invention are especially useful for a patient suspected of being at risk for developing a disease associated with an altered expression level of presenilin 2 proteolytic fragments based on family history, or a patient in which it is desired to diagnose a presenilin 2 proteolytic fragment-related disease (ex. familial Alzheimer's Disease (FAD)).

According to the invention, presymptomatic screening of an individual in need of such screening is now possible using antibodies which bind specifically to the herein-described presenilin 2 proteolytic fragments.

In one preferred embodiment of the method of screening, a tissue sample would be taken from such individual, and screened for the presence of presenilin 2 protein and presenilin 2 proteolytic fragments. Presenilin 2 proteolytic fragments can be (a) detected and/or (b) quantitated using a biological assay for presenilin 2 proteolytic fragment activity or using an immunological assay and presenilin 2 proteolytic fragment antibodies. When assaying presenilin 2 proteolytic fragments, the immunological assay is preferred for its speed. An aberrant presenilin 2 proteolytic fragment level would indicate that the patient is at risk for developing a presenilin 2 proteolytic fragment-associated disease.

The present invention is described in further detail in the following non-limiting examples.

EXAMPLES

The following protocols and experimental details are referenced in the examples that follow.

Materials

Tetracycline and ALLN (N-acetyl-L-leucinal-L-norleucinal) were purchased from Sigma. Lactacystin was supplied by Dr. E. J. Corey (Harvard University, Cambridge, Mass.). Other protease inhibitors and high quality Triton X-100 were purchased from Boehringer Mannheim. Brefeldin A (BFA) was pruchased from Calbiochem.

Fusion Proteins and Antibodies

The glutathione S-transferase fusion protein encoding the large hydrophilic loop domain of PS2 was generated as described (Thinakaran, G., et al., Neuron 17:151–190 (1996)). For some experiments, the GST fusion protein encoding the large hydrophilic loop domain of PS2 and the αPS2Loop and αPS1Loop polyclonal antisera were kindly provided by Gopal Thinakaran and Sam Sisodin (Thinakaran, G., et al., Neuron 17:181–190 (1996)). Anti-PS2Loop is a polyclonal antiserum generated by immunizing rabbits with gel-purified human PS2 loop fusion protein. Monoclonal (M2) and polyclonal (D-8) antibodies raised against FLAG peptide (DYKDDDDK) (SEQ ID NO: 15) were purchased from IBI and Santa Cruz Biotechnology, respectively. Mouse monoclonal antiubiquitin antibody (Ubi-1) was purchased from Zymed Laboratories, Inc. Rabbit polyclonal anti-ubiquitin antibodies were purchased from Sigma. Monoclonal antibodies to PARP and CPP32 were purchased from Pharmigen and Transduction Laboratories, respectively. Goat anti-HSP70 antibody was purchased from Santa Cruz Biotechnology.

Generation of Founder Cell Line for an Inducible Expression System

Founder cell lines were generated by co-transfecting H4 neuroglioma cells in a 100-mm dish with 10 μg of pUHDI5-1, a plasmid encoding a tetracycline-repressible transactivator (Gossen, M., and Bujard, H., Proc. Natl. Acad. Sci. USA 89:5547–5551 (1992)) and 1 μg of pCMVneo. Individual G418-resistant colonies were isolated and characterized by transient transfection with the luciferase reporter plasmid pUHC13-3, whose promoter is induced by the transactivator. Luciferase induction in the presence and absence of tetracycline was measured by Western blot analysis using anti-luciferase antibody (Progema) to identify cells with maximal indicibility and tight regulation.

Preparation of cDNA Constructs

The cDNAs for wild-type PS2 were subcloned from the pcDNA3 construct (Kovacs, D. M., et al., Nat. Med. 2:224–229 (1996)) into the tetracycline-inducible expression plasmid pUHD10-3 vector using polymerase chain reaction by Pfu polymerase (Stratagene). FLAG epitopes were added to either 5' or 3' ends of PS2 using polymerase chain reaction with the coding sequence for fusion to the sequence, DYKDDDDK (SEQ ID NO: 15). Resulting constructs, PS2s with either 3° FLAG or 5° FLAG peptides, were verified by DNA sequencing.

Generation of Stably Transformed Cell Lines with Inducible PS2 Constructs

The H4 founder cells were transfected with 10 μg of each construct and 1 μg of pCNH2hygro, conferring resistance to hygromycin. Hygromycin-resistant colonies were isolated in the presence of tetracycline and screened for PS2 expression by Western blot analysis using antibodies against the FLAG epitope-tag upon removal of tetracycline. For each PS2 construct, five classes demonstrating various induction levels with tight regulation by tetracycline were selected and used for further study. For induction of PS2, cells were washed five times with prewarmed phosphate-buffered saline to retrieve residual tetracycline and then incubated with complete media without tetracycline for the indicated hours.

Cell Fractionation

Cells were fractionated into detergent-soluble and resistant fractions with CSK buffer (10 mM PIPES (pH 6.8), 100 mM NaCl, 2.5 mM MgCl$_2$, 1 mM CaCl$_2$, 0.3 M sucrose, 1% Triton X-100, 1 mM phenylmethysulfonyl fluoride, 1 μg/ml aprotinin, 1 μg/ml chymostatin, 1 μg/ml leupeptin, 1 μg/ml pepstatin A) (Papadopoulos, V., and Hall, P. F., J. Cell. Biol. 108:553–567(1989)). Cells were washed with ice-cold phosphate-buffered saline and incubated in CSK buffer for 5 min on ice with gentle rocking. The supernatant (detergent-soluble fraction) was collected, and the insoluble structure that remained on the dish was collected, washed one with CSK buffer, and used as detergent-insoluble fraction. The resulting detergent-resistant pellet which consists primarily of cytoskeletal proteins was further incubated with DNase (300 μg/ml) (Papadopoulos, V., and Hall, P. F., J. Cell. Biol. 108:553–567 (1989); Hamaguchi, M., and Hanafusa, H., Proc. Natl. Acad. Sci. USA 84:2312–2316 (1987); Osborn, M., and Weber, K., Exp. Cell Res. 106:339–349 (1977)).

Nickel Affinity Chromatography

PS2 cells were transiently transfected with ubiquitin constructs either pCW7 (H6M-Ub) or pCW8 (H6M-UbK48R) using LipofectAMINE™ according to the manufacturer's instruction (LifeTtechnologies, Inc.). The detergent lysate was prepared in ice-cold buffer (10 mM Tris-HCl (pH 7.4), 1% Triton X-100 containing protease inhibitors (2 mM Pefabloc SC, 5 μg/ml ALLN, 1 μg/ml aprotinin, 1 μg/ml leupeptin, 1 μg/ml pepstatin A, 50 pg/ml N-p-tosyl-L-lysine chloromethyl ketone, and 50 μg/ml L-1-tosylamido-2-phenylethyl chloromethyl ketone) from the confluent 100-mm dish. To detect 6× His-tagged PS2, the detergent-soluble fraction was incubated with nickel-nitrilotriacetic acid spin column (Quiagen, Hilden, Germany) overnight and washed extensively, and bound materials were eluted by passing elution buffer (1 M imidazole, 50 mM phosphate buffer (pH 6.0), 300 mM NaCl, 0.5% Triton X-100) twice through the spin column. Samples were concentrated by freeze-drying, and PS2 immunoreactivity was detected by Western blotting using anti-PS2Loop antibodies.

Western Bloting and Immunoprecipitation

Protein samples were quantiated by the BCA protein assay kit (Pierce). SDS-PAGE was carried out using 4–20% gradient Tris-glycine gels under reducing conditions. Proteins were transferred to polyvinylidene difluoride membrane (Bio-Rad) using a semi-dry electrotransfer system (Hoefer). The blots were blocked with 5% non-fat dry milk in TBST (25 mM Tris (pH 7.6), 137 mM NaCl, 0.15% Tween 20) for 1.5 h, incbated primary antibodies (M2, 3 µg/ml; D-8, 1 to 1000; polyclonal anti-ubiquitin, 1 to 1000; Ubi-1, 1 to 1500) for 1.5 h, and secondary antibodies (horseradish perodixase-conjugated anti-mouse or rabbit antibodies, 1 to 5000) in TBST. Between steps, the blots were washed with TBST for 30 min. For Western blotting with M2 antibodies, 5% (w/v) non-fat dry milk was included in the incubation steps for primary and secondary antibodies. The blot was visualized using the ECL Western blot detection system (Amersham). For immunoprecipitation, cells were lysed using IP buffer (10 mM Tris-HCl (pH 7.4), 150 mM NaCl, 1% Triton X-100, 0.25% Nonidet P-40, 2 mM EDTA) plus protease inhibitors, and solubilized proteins were subjected to immunoprecipitation. The samples were precleared with protein A conjugated with magnetic beads (Perceptive Diagnosis) for 1 h in the cold room, incubated with either control (rabbit anti-mouse IgG) or anti-FLAG (D-8 at 10 µg/ml) antibodies overnight, further incubated with protein A-magnetic beads (30 µl/sample) for 2 h in the cold room, and washed three times with IP buffer. Immunoprecipitates were collected using a magnetic bead collector, boiled in sample buffer, and subjected to SDS-PAGE and Western blotting using monoclonal anti-ubiquitiin antibodies.

For some experiments, protein quantitation, SDS-PAGE (4–20% or 16%) and Western blotting were carried out as described, supra, with the exception of using the lysis buffer (10 mM Tris-HCl [pH 7.4], 150 mM NaCl, 1% Triton X-100, 0.5% NP-40, 5 mM EDTA plus either 0.3% SDS or 1% Sarkosyl) with protease inhibitors, allowing for the efficient extraction of the 20 kDa C-terminal fragment from the detergent-resistant fractions.

Site-Directed Mutagenesis, cDNA Constructs, and Inducible PS1 Cells

The point mutations in the potential aspartate cleavage sites of PS2 (D326A and D329A) and control aspartate (D308A) were introduced into a PS2 open reading frame by site-directed mutagenesis using Muta-Gene phagemid kit (BioRad). The inducible construct encoding the full-length PS1 with 3' FLAG epitope sequence was generated as described for PS2 herein. To establish the inducible PS1 cells, the resulting constructs were sequenced and stably transfected into the H4 human neuroglioma founder cell line as described herein for the PS2 inducible cell.

Example 1

Endoproteolytic Processing of PS2

Figures 1, 5A:
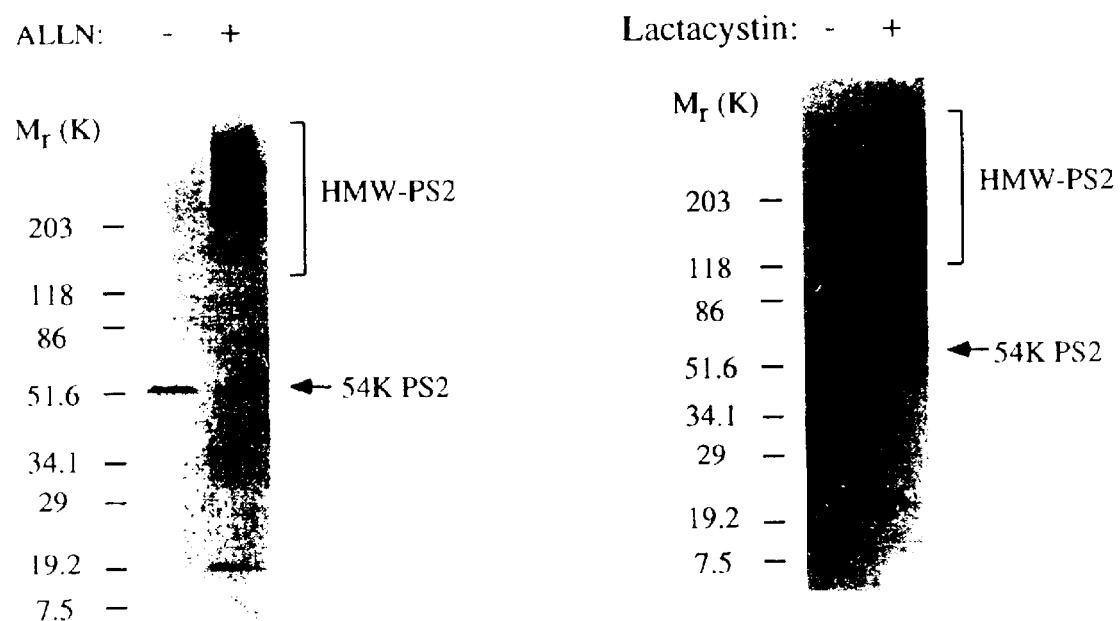
FIG. 1. Inducible expression and endoproteolytic cleavage of PS2. Detection of C- and N-terminal PS2-derived cellular fragments. Western blot analysis of SDS lysates prepared from stably transformed, PS2-inducible H4 human neuroglioma cells grown in the presence (1 µg/ml) or absence of tetracycline for 48 h. PS2-inducible lines were established using the tetracycline-repressible transactivator (Gossen, M., and Bujard, H., *Proc. Natl. Acad. Sci. USA* 89:5547–5551 (1992)). The presence of tetracycline in the culture medium suppresses PS2 expression, while its withdrawal results in induction of PS2 expression. H4 neuroglioma founder cells were stably transfected with constructs encoding full-length PS2 fused with FLAG epitope peptide in C terminus (clone: WF26.
FIG. 5A) inhibition of PS2 degradation by the 20 S proteasome inhibitors, ALLN and lactacystin. Wild-type PS2-expressing cells (clone WF2: C-terminal FLAG) were induced for 12 h and further incubated with ALLN (50 µM) or lactacystin (10 µM) for an additional 12 h. Detergent-soluble (Soluble) and detergent-resistant fractions (Insoluble) were prepared and analyzed by Western blotting.

To investigate the processing pathway of PS2, a regulated system for the expression of PS2 was established. For this purpose, inducible H4 cell lines expressing epitope-tagged versions of wild-type PS2 using a tetracycline-repressible transactivator were developed (Gossen, M., and Bujard, H., Proc. Natl. Acad. Sci. USA 89:5547–5551 (1992)). In this system, the presence of tetracycline in the culture medium suppresses PS2 expression, while its withdrawal results in induction of PS2 expression. PS2 production following induction was monitored by Western blot analysis using antibodies against either N-terminal or C-terminal FLAG epitope tags or using a polyclonal antisera specific for the large hydrophilic loop (HL-6) of PS2 (αPS2Loop). FIG. 1 shows the results of Western blot analysis of a cellular lysate from representative, stably transformed cell lines expressing wild-type PS2 grown in the presence or absence of tetracycline for 48 h. No PS2 was observed for cell lines incubated in tetracycline-containing media, indicating the tight regulation of PS2 expression in this system. The SDS-extracted proteins detected by the monoclonal anti-FLAG antibody, M2, included full-length PS2 with an apparent molecular mass of 54 kDa and high molecular mass species of PS2 (HMW-PS2; FIG. 1) for both N- and C-terminal FLAG-tagged PS2. In addition, a C-terminal 20 kDa fragment (PS2-CTF) and an N-terminal 34 kDa fragment (PS2-NTF) were observed (FIG. 1), indicating that PS2 undergoes endoproteolytic cleavage like its homologue, PS1 (Thinakaran, G., et al., Neuron 1 7:151–190 (1996)). Both the N-terminal and C-terminal fragments appeared to be stable cellular products as opposed to degradation products since their presence was not affected by the absence of protease inhibitors in the lysis buffer, and they were not affected by prolonged incubation for up to 12 h at 37° C. These results reveal a 54-kDa PS2 protein that undergoes endoproteolytic cleavage to generate 34-kDa N-terminal and 20-kDa C-terminal fragments. The generation of the PS2 endoproteolytic fragments could either be a step in the metabolic pathway of PS2 and/or a processing event necessary for the normal function of PS2.

Example 2

Detergent Solubility of PS2 Fragments

Figure 2B:
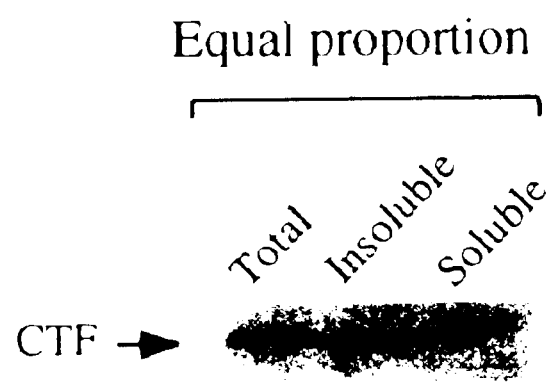

The detergent solubility of the N-terminal and C-terminal endoproteolytic fragments was compared. 48 h after induction, a comparison of equal amounts of proteins from the detergent (1% Triton X-100)-soluble and insoluble fractions revealed the PS2-NTF only in the soluble fraction, while the PS2-CTF was enriched in the detergent-resistant fraction (FIG. 2). Loading of equal volumes of the soluble and insoluble fractions, normalized for total cellular proteins, revealed a small amount of PS2-CTF in the soluble fraction, but the majority of the gragment localized to the insoluble fraction. The enrichment of the PS2-CTF with the detergent-resistant cellular fraction (FIG. 2) prepared by a procedure classically employed to isolate either detergent-resistant cytoskeletal structures (Papadopoulos, V., and Hall, P. F., J. Cell. Biol. 108:553–567 (1989); Hamaguchi, M., and Hanafusa, H., Proc. Natl. Acad. Sci. USA 84:2312–2316 (1987); Osborn, M., and Weber, K., Exp. Cell Res. 106:339–349 (1977); Rafolo, L. M., et al., J. Neurosci 11:3888–3897 (1991); Allinquant, B., et al., J. Neurosci. 14:6842–6854 (1994)) or caveolae-like microdomains (Sargiacomo, M., et al., J. Cell Biol. 122:789–807 (1993); Gorodinak, A., and Harris, D. A., J. Cell Biol. 129:619–627 (1995); Li, S., et al., J. Biol. Chem. 270:15693–15701 (1995)) suggests that the PS2-CTF may be a component of one of these cellular structures. Alternatively, this association could be due to the formation of detergent-resistant HMW-PS2 complexes which localize to this fraction. The detergent insolubility of the PS2-CTF is unlikely to be due to the presence of the FLAG epitope since the PS2-CTF cleaved from the PS2 containing the N-terminal FLAG was also enriched in the detergent-resistant cellular fraction.

Example 3

Induction and Turnover of PS2

Figure 3A:
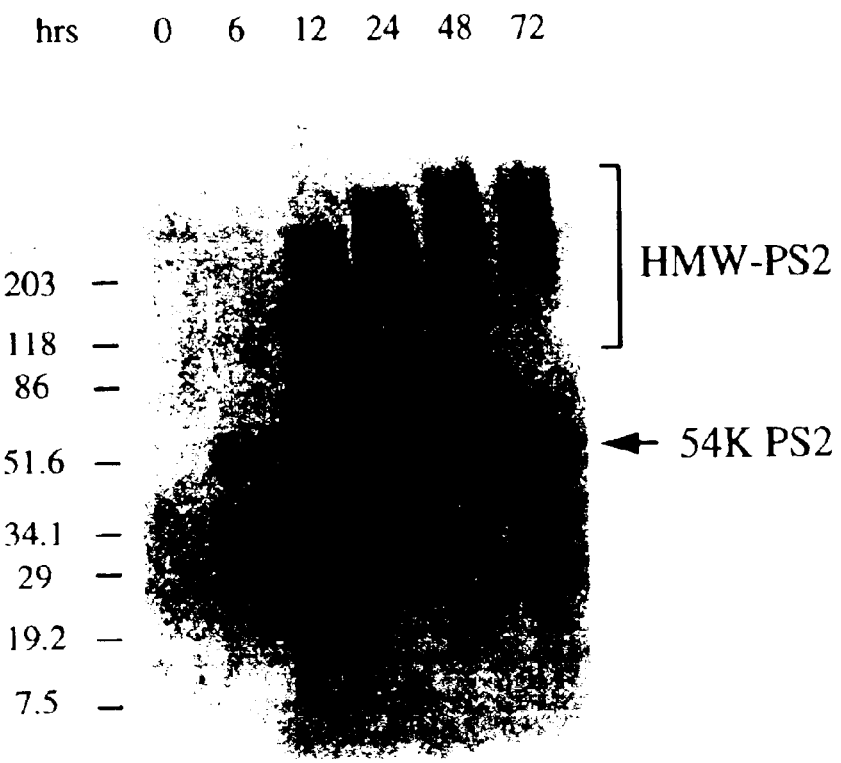
FIG. 3. Time course of PS2 induction. Inducible PS2 cells (clone WF2) were grown in the absence of tetracycline and harvested at timed intervals up to 72 h. Equal amounts of proteins (30 µg) from detergent-soluble (FIG. 3A) and detergent-resistant fractions (FIG. 3B) were analyzed by Western blotting to detect the 54K PS2, HMW-PS2, and 20K CTF. The 54K PS2 and HMW-PS2 were extractable by the detergent treatment.
Figure 3B:

Inducible PS2 cell lines were induced and harvested at time intervals up to 72 h. Equal amounts of protein were then analyzed from the detergent-resistant and detergent-soluble fractions (FIG. 3). PS2 carrying the C-terminal FLAG was first detected in the detergent-soluble fraction at 6 h post-induction as a full-length 54-kDa band. Thereafter, increasing amounts of HMW-PS2 were observed along with the appearance of a doublet owing to the presence of a band just below the 54-kDa band. By 72 h post-induction, the lower band of the doublet was not observed, and both the HMW-PS2 and the 54-kDa PS2 bands were less abundant relative to 48 h post-induction. In the detergent-resistant fraction, no obvious PS2 signal was detected by anti-FLAG antibody until 48 h post-induction at which point the PS2-CTF was observed. However, in "high"-expressing PS2 clonal cell lines (e.g., WF9), the PS2-CTF could be observed as early as 24 h post-induction.

Figure 4A:
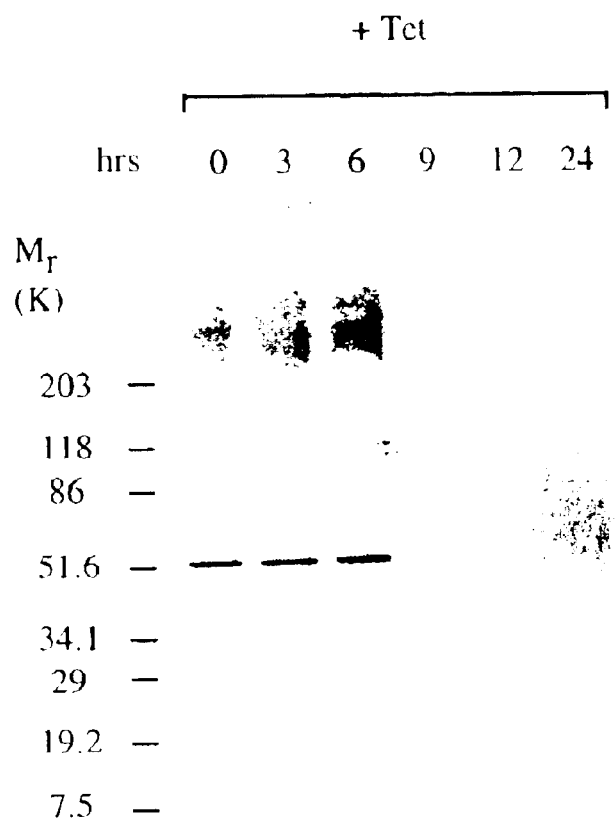
FIG. 4. Turnover of PS2 in the inducible system. H4 transfectants with C-terminal FLAG PS2 constructs (clone: WF9) were grown in the absence of tetracycline for 36 h. To measure PS2 turnover in this system, tetracycline was added back to the culture medium at 36 h post-induction (indicated as time 0), and detergent-soluble and detergent-resistant fractions were prepared at timed intervals up to 24 h and analyzed by Western blotting. Turnover of wild-type 54K PS2 and HMW-PS2 present in the detergent-soluble fraction is shown in FIG. 4A, and metabolism of 20-kDa C-terminal fragments in the detergent-resistant fraction is shown in FIG. 4B. Equal amounts of proteins were loaded in each lane.
Figure 4B:
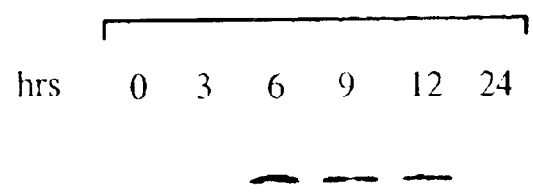

The inducible system was next employed to examine the turnover of PS2 containing the C-terminal FLAG (FIG. 4). PS2 was induced for 36 h, and PS2 turnover was assessed by adding tetracycline back to the media to repress further PS2 production (time point 0) and then testing detergent-soluble and detergent-resistant cellular fractions at timed intervals up to 24 h. Levels of HMW-PS2 and full-length 54-kDa PS2 were observed to progressively decrease over time and were largely undetectable after 24 h and 9 h post-repression, respectively, in the soluble fraction. In the detergent-resistant fraction, the PS2-CTF was observed as a highly stable fragment which remained relatively stable over the degradation time course. These data suggest that following cleavage the PS2-CTF is translocated to the detergent-resistant fraction where it exists as a relatively stable polypeptide.

Example 4

Degradation of PS2 by the Proteasome Pathway

To further investigate the degradation of PS2, the effects of a set of known cell-permeable protease inhibitors on the degradation of PS2, including pepstatin A, Pefabloc SC, E-64, leupeptin, and aprotinin were tested. None of these protease inhibitors affected the turnover of the PS2-CTF. Next, PS2 was tested to determine whether it is polyubiquitinated and degraded by the ubiquitin-proteasome pathway (Hochstrasser, M., Curr. Opin. Cell Biol. 7:215–223 (1995); Hochstrasser, M., Cell. 84:813–815 (1996); Ciechanover, A., Cell 79:13–21 (1994); Finley, D., and Chau, V., Annu. Rev. Cell Biol. 7:25–69(1991)). For this purpose, the proteasome inhibitors, ALLN and lactacystin (Fenteany et al., Science 268:726–771 (1994)) were used, which are known to induce the accumulation of polyubiquitinated proteins by inhibiting the 20 S proteasome (the catalytic core of the 26 S complex) (Rock, K. L., et al., Cell 78:761–771 (1994); Ward, C. L., et al., Cell 83:121–137 (1995); Jensen, T. J., et al., Cell 83:129–135 (1995)). Treatment with ALLN and lactacystin resulted in dramatically increased levels of HMW-PS2 while only full-length PS2 was observed in the absence of proteasome inhibitors (FIG. 5A).

Figure 5B:
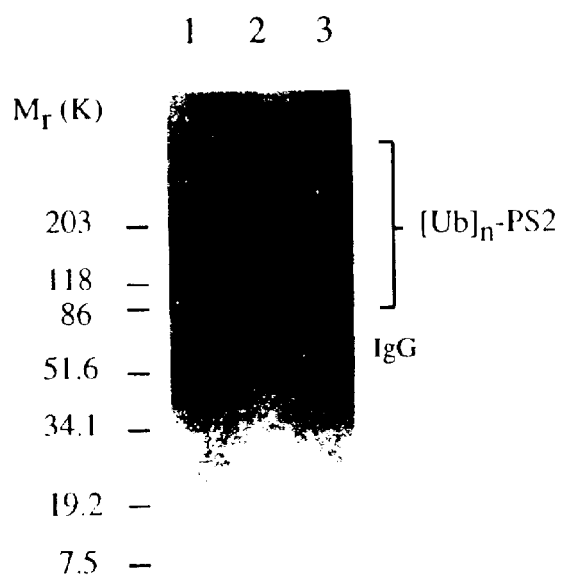
FIG. 5B) immunoprecipitation of ubiquitin-positive high molecular weight forms of PS2 (HMW-PS2) by anti-FLAG antibodies. Stable cells expressing C-terminal epitope-tagged PS2 (clone WF9) were incubated for 24 h in the tetracycline-absent media either without (lane 2) or with (lane 3) 40 µM ALLN and were lysed using IP buffer, and soluble proteins were immunoprecipitated with control (rabbit anti-mouse IgG; lane 1) or polyclonal (D-8) anti-FLAG antibodies (lanes 2 and 3), Immunoprecipitates were separated on 4–20% SDS-PAGE, and polyubiquitinated PS2 ([Ub1-PS2) was detected by Western blot analysis using monoclonal (Ubi-1) ubiquitin antibody. FIG. SC) binding of PS2 modified with epitope-tagged ubiquitin (H6M-Ub) to nickel affinity columns. Plasmid pCW7 encoding wild-type (H6M-Ub) or pCW8 encoding dominant-negative ubiquitin (H6M-UbK48R) was transiently transfected into uninduced PS2 cells (clone WF2). Transiently transfected PS2 cells were either uninduced (lanes 1, 3, 5, 7, 9, and 11) or induced for 12 h (lanes 2, 4, 6, 8 10, and 12) in the absence (lanes 1–6) or presence of (lanes 7–12) ALLN. Lysates were subjected to nickel affinity chromatography as described herein and bound materials were analyzed by Western blotting using anti-PS2Loop antibodies.

To further explore the possibility that the HMW-PS2 contained polyubuquitinated PS2, PS2 containing the C-terminal FLAG was immunoprecipitated using polyclonal anti-FLAG antibodies and subjected to immunoblot analysis with a monoclonal anti-ubiquitin antibody (FIG. 5B). Ubiquitin-positive HMW-PS2 was detected and found to be significantly increased following treatment with 50 $\mu$M ALLN. These findings were also confirmed using additional monoclonal anti-FLAG and polyclonal anti-ubiquitin antibodies.

To determine whether polyubiquitinated HMW-PS2 serves as a degradation intermediate for the full-length PS2, constructs encoding wild-type (H6M-Ub) and dominant-negative ubiquitin (H6M-UbK48R), tagged with poly((6X)-histidine) were transiently transfected into uninduced cells. Lysates from PS2 cells that were either uninduced or induced for 12 h (when the predominant species is full-length PS2 and not HMW-PS2; FIG. 3) in the presence or absence of ALLN were then subjected to nickel affinity chromatography, and bound products (ubiquitinated proteins) were subjected to immunoblot analysis with the αPS2Loop antibody (FIG. 5C). In the cells which were not treated with ALLN, no polyubiquitinated HMW-PS2 was observed with the exception of a small amount in one lane (FIG. 5C, lane 6) where dominant-negative ubiquitin was transferred into PS2-expressing cells. In contrast, induced cells which were treated with ALLN and were transiently transfected with H6M-Ub revealed abundant amounts of polyubiquitinated HMW-PS2 (FIG. 5C, lane 10). Meanwhile, the induced cells which were treated with ALLN and were transiently transfected with dominant-negative mutant H6M-UbK48R revealed a small amount of polyubiquitinated HMW-PS2 (FIG. 5C, lane 12) similar to the amount observed in lane 6. These findings indicate that full-length PS2 can be modified by epitope-tagged ubiquitin in vivo to form ubiquitinated HMW-PS2 and degraded through the ubiquitin-proteasome pathway. Thus, polyubiquitinated HMW-PS2 likely serves as an intermediate for full-length PS2 degradation in this system.

Figure 6:
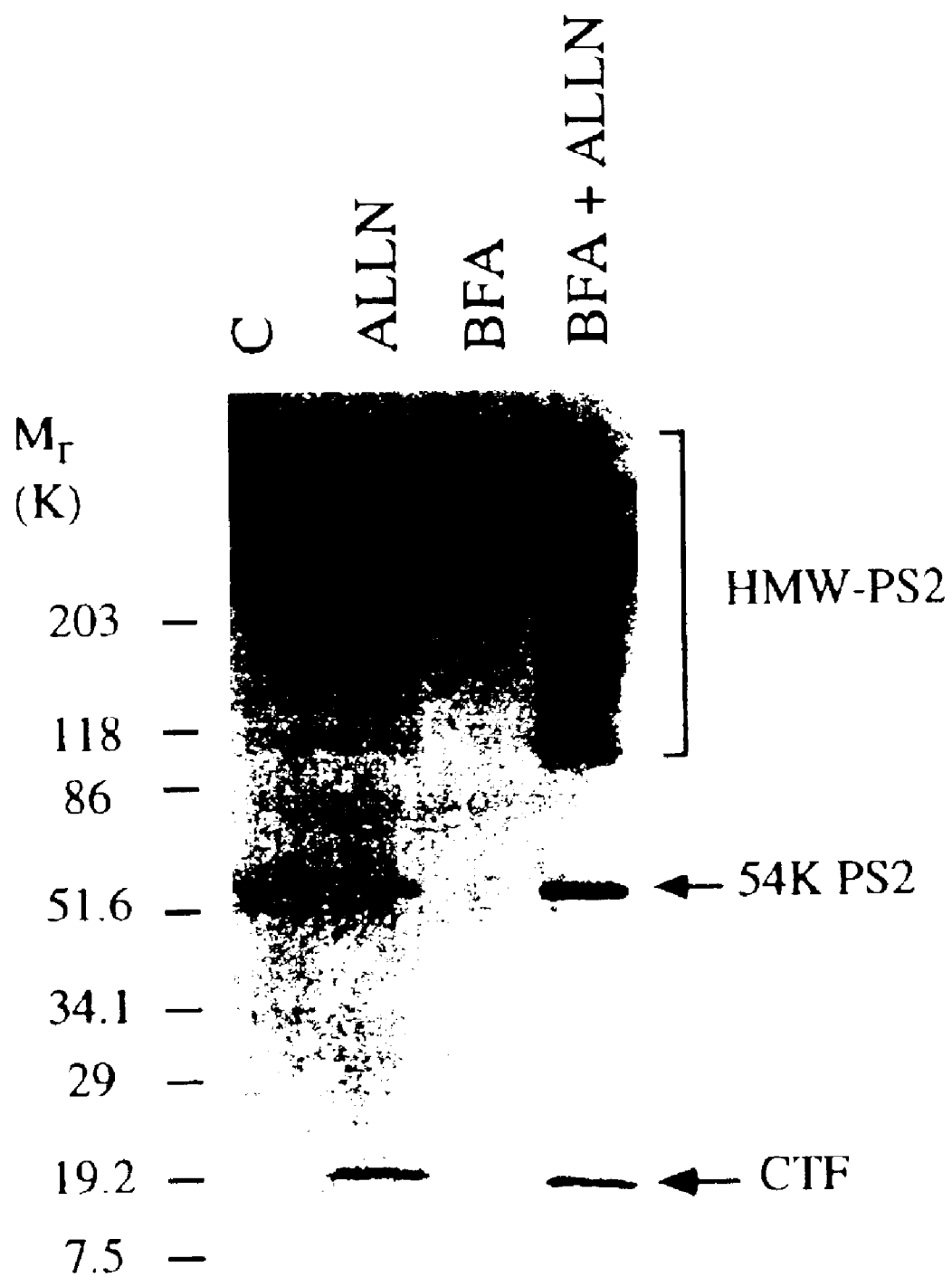
FIG. 6. Effect of BFA on the ER degradation of PS2. Inducible wild-type PS2 cells (clone WF2) were grown in the absence of tetracycline for 12 h and were further incubated for an additional 12 h with ALLN (50 µM), BFA (5 µg/ml), and ALLN plus BFA.

To determine the cellular site for polyubiquitination and proteasomal degradation of PS2, the effects of BFA were tested. BFA is known to induce the disassembly of the Golgi complex and lead to rapid degradation of full-length PS2 (FIG. 6). However, treatment with both BFA and ALLN resulted in even greater accumulation of HMW-PS2 than with ALLN alone, while no significant increase was observed for PS2-CTF (FIG. 6). Similar results were obtained using lactacystin (data not shown). These results suggest that polyubiquitination and proteasomal degradation of PS2 occur in a pre-Golgi compartment (e.g ER). These data also indicate that the generation and accumulation of the PS2-CTF may be regulated by additional proteolytic enzymes located in other subcellular sites.

The ubiquitin-proteasome pathway is known to play a role in the selective turnover of intracellular protein substrates via complete degradation. However, this pathway also participates in the functional alteration of specific proteins by limited proteolysis or endocytosis following polyubiquitination (for review, see Hochstrasser, Curr. Opin. Cell Biol. 7:215–22(1995); Hochstrasser, Cell 84:813–815(1996); Ciechanover, Cell 79:13–21 (1994); and Finley and Chau, Annu. Rev. Cell Biol. 7:25–69 (1991)). The proteasome has been shown to degrade ER proteins (Wiertz, E. J. H. J., et al., Nature 384:482–488 (1996)). Thus, the ubiquitination and subsequent degradation of PS2 by the proteasome pathway serve as a means for regulating the turnover of PS2 in the ER. The ubiquitin-proteasome pathway is also utilized in the transfected cells to dispose of excess PS2 thereby regulating the amount of PS2 that is available for endoproteolysis. Since there are extremely low levels of endogenous full-length PS1 (Thinakaran, G., et al., Neuron 17:151–190 (1996)) and PS2 (Kim, T. -W., et al., Soc. Neurosci. Abstr. (1996)), the proteasome may also play a role in regulating full-length presenilin degradation endogenously. It is unlikely, however, that the proteasome carries out the endoproteolytic cleavage of PS2 into the NTF and CTF since proteasome inhibitors did not block the generation of these fragments (FIGS. 5A and 6). Two ER proteins that have been shown to be degraded by an ALLN/lactacystin-sensitive proteasomal pathway are 3-hydroxy-3- methylglutaryl-coenzyme A reductase (Inoue, S., et al., *J. Biol. Chem.* 266:13311–13317 (1991); McGee, T. P., et al., *J. Biol. Chem.* 271:25630–25638 (1996)) and the sterol regulatory element-binding protein (Sakai, J., et al., *Cell* 85:1037–1046 (1996); Wang, W., et al., *Cell* 77:53–62 (1994)). Interestingly, 3-hydroxy-3methylglutaryl-coenzyme A reductase, a key regulatory enzyme of cholesterol biosynthesis, has been shown to span the membrane eight times (Roitelman et al., *J. Cell. Biol.* 117:959–973 (1992)), similar to the topological model recently proposed for PS1 (Li, X, and Greenwald, I., *Neuron* 17:1015–1021 (1996); Doan, A., et al., *Neuron* 17:1023–1030 (1996)). Thus, PS2 is now the second putative eight-transmembrane domain protein which has been localized to the ER (Kovacs, D. M., et al, *Nat. Med.* 2:224–229 (1996); Cook, D. G., *Proc. Natl. Acad. Sci. USA* 93:9223–9228 (1996); Walter, J., et al., *Mol. Med* 2:673–691 (1996)) and is degraded by the proteasomal pathway.

These data show that PS2 expressed in transfected H4 cell lines undergoes endoproteolytic cleavage, is ubiquitinated, and degraded via an ALLN/lactacystin-sensitive proteasome pathway. Although it is unclear how aberrations in the metabolism of the presenilins ultimately lead to altered processing of APP and increased production of Aβ42, conformational changes of presenilins due to FAD mutations could conceivably alter their metabolism and adversely affect the processing of APP.

Example 5

Figures 1, 7D:
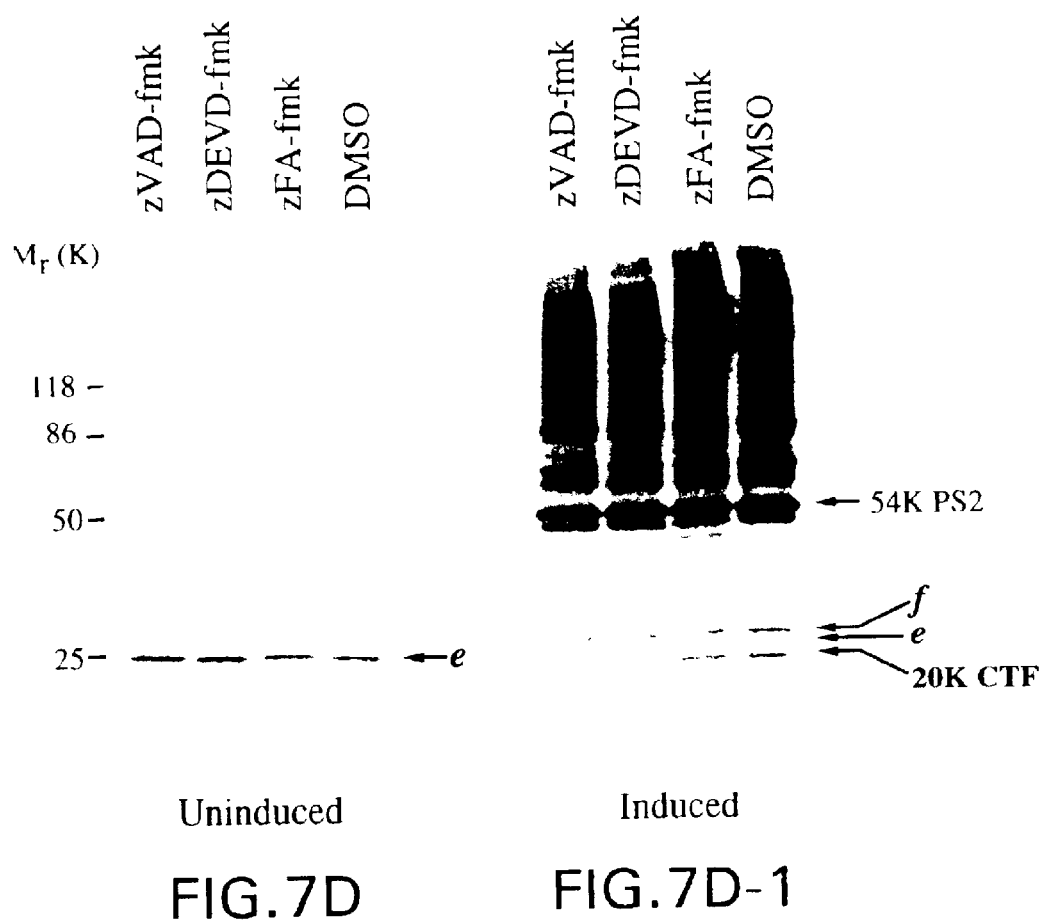

Apoptotic Cleavage of Alzheimer-Associated Presenilins by a CPP332-Like Protease Apoptosis (programmed cell death) is an evolutionary conserved form of cellular suicide which plays a beneficial role during development and homeostasis (Jacobson, M. D., et al., *Cell* 88:347–354 (1997)). Extensive evidence indicates that activation of apoptotic cell death is associated with a variety of neurodegenerative disorders (Thompson, C. B., *Science* 267:1456–1462 (1995)) including Alzheimer's disease (AD) (Johnson, E. M., *Neurobiol. Aging* 15:5187–5189 (1994); Cotman, C. W. and Anderson, A. J., *Mol. Neurobiol.* 10:19–45 (1995); LeBlanc, A., "Apoptosis and Alzheimer's Disease," in *Molecular Mechanism of Dementia*, Humana Press, Totowa, N.J. (1996), pp. 57–71). Overexpression of PS1 and PS2 has been reported to lead to apoptosis in transfected cells (Wolozin, B., et al, *Science* 274:1710–1713 (1996); Gao, Q., et al., *NeuroReport* 8:379–383 (1996); Deng, G., et al., *FEBS Lett.* 397:50–54 (1996)). Whether the presenilins serve as substrates for apoptosis-associated cleavage in the programmed cell death pathway was examined. For this purpose, the endogenous form of the PS2 endoproteolytic C-terminal fragment (CTF) was identified in human brain homogenate utilizing αPS2Loop, αPS2-specific antibody raised against the large hydrophilic loop domain following predicted transmembrane domain six of PS2. The endogenous PS2-CTF appeared as a 25 kDa band in both human brain (FIG. 7a) and in uninduced H4 neuroglioma cells (FIG. 7b, net+). As has been reported for PS1 (Thinakaran, G., et al., *Neuron* 17:181–190 (1996)), no full-length PS2 was detected in brain (FIG. 7a) or in uninduced cells (FIG. 7b).

In H4 cells that were induced to overexpress PS2 containing a C-terminal FLAG epitope tag (FIG. 7b, tet–), the 54 kDa full-length and high molecular weight forms of PS2 were observed along with multiple CTF with apparent molecular weights of 26 kDa, 25 kDa and 20 kDa. The 26 kDa and 20 kDa CTF were absent in the uninduced samples (FIG. 7b), and could be immunoprecipitated with anti-FLAG antibodies, indicating that these fragments were derived from the PS2 transgene. The 26 kDa fragment is most likely the normal 25 kDa cleavage product plus the eight amino acid FLAG epitope tag. As has been previously shown for PS1 (Thinakaran, G., et al., *Neuron* 1 7:181–190 (1996)), the generation of the normal PS2-CTF appears to be a regulated endoproteolytic event. This is evidenced by the observation that levels of the 26 kDa transgene-derived PS2-CTF were not considerably greater than those of the native 25 kDa CTF in the uninduced cells. Additionally, levels of the native 25 kDa CTF were diminished in the induced cells, suggesting that the production of the transgene-derived CTF led to an attenuation in the amount of endogenous CTF. A similar type of "replacement" phenomenon has previously been reported to PS1 in transgenic mice expressing human PS 1 (Thinakaran, G., et al., *Neuron* 17:181–190 (1996)).

In contrast, the alternative 20 kDa PS2-CTF did not appear to be generated in a regulated fashion. It was shown, supra, that overexpression of PS2 in transfected cells also leads to the generation of a 20 kDa CTF which predominantly localizes to the detergent-resistant cellular fraction, and which exhibits a very slow rate of turnover. The regulated 26 kDa normal cleavage product was not detectable on Western blots using the relatively insensitive anti-FLAG antibody. In the present example using a sensitive αPS2Loop antibody, while the endogenous (arrow e) and normal transgene-derived (arrow f) CTFs were primarily localized to the detergent-soluble fraction (FIG. 7c, lane 3), the smaller alternative 20 kDa CTF was enriched in the detergent-resistant fraction (FIG. 7c, lane 2). Together, these data indicate that when overexpressed in stably-transfected H4 cells, PS2 is cleaved at a site which is located distal to the normal cleavage site, resulting in a smaller detergent-insoluble CTF.

Next, the protease responsible for generating the 20 kDa CTF was identified. Given recent reports that overexpression of PS2 induced apoptosis in transfected cells (Wolozin, B., et al., *Science* 274:1710–1713 (1996); Deng, G., et al., *FEBS Lett.* 397:50–54 (1996)), the effects of zVAD, a broad-spectrum inhibitor for most mammalian interleukin-1β converting enzyme ICE/Ced-3 proteases (caspases), and zDEVD-fmk, a selective inhibitor for CPP32-like proteases (CPP32, Mch2, and Mch3) (Martin, S. J. and Green, D. R., *Cell* 82:349–352 (1995); Chinnaiyan, A. M. and Dixit, V. M., *Curr. Biol.* 6:555–562 (1996)) were tested. Both zVAD and zDEVD blocked the generation of the 20 kDa PS2-CTF (FIG. 7d) but had no effect on levels of the endogenous 25 kDa CTF (FIG. 7d, arrow e), the 26 kDa transgene-derived CTF (FIG. 7d, arrow f), or other PS2 species. These findings suggest that in the absence of traditional apoptotic stimuli, overexpression of PS2 led to the activation of CPP32-like proteases which alternatively cleaved PS2.

Figure 8:
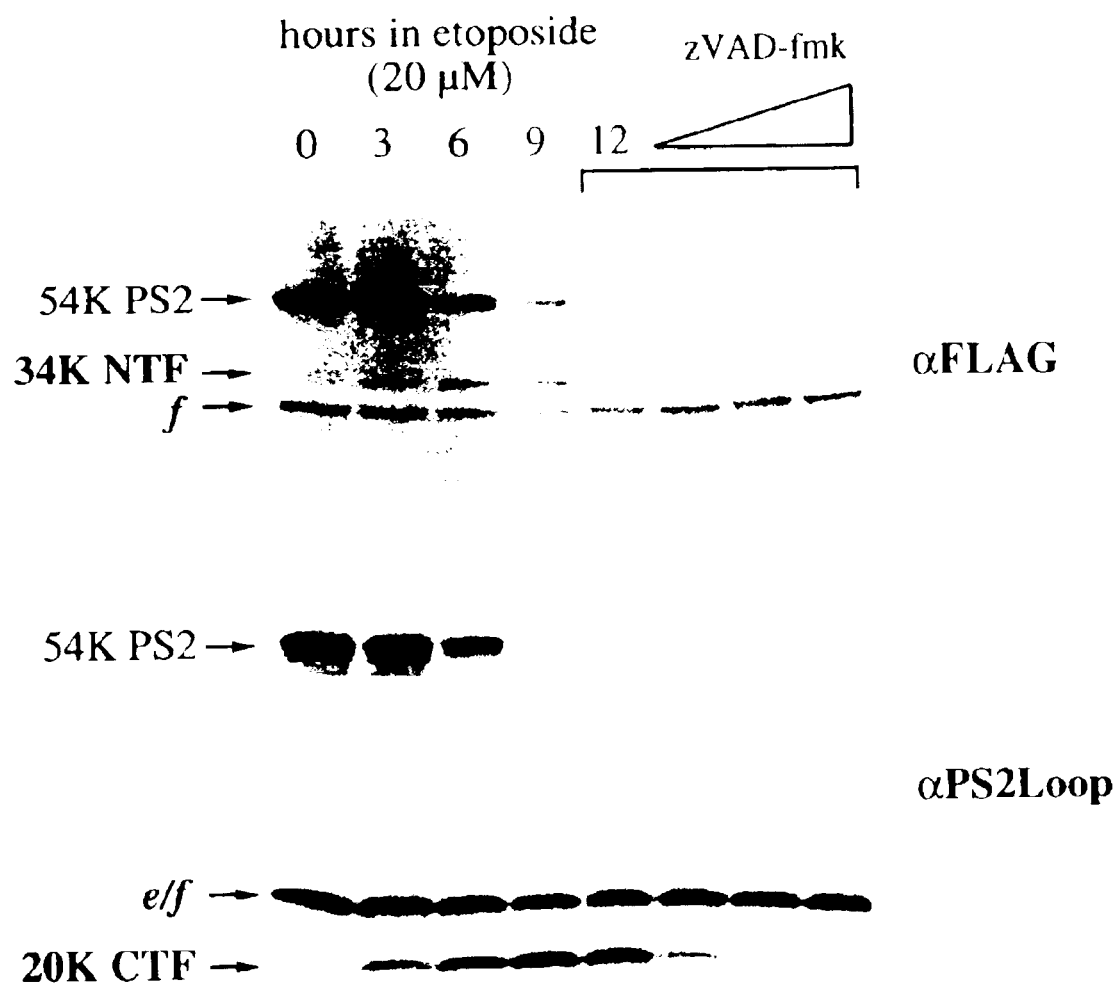
FIG. 8. Cleavage of full-length 54 kDa PS2 by a zVAD-sensitive protease activated during etoposide-induced apoptosis. Inducible H4 cells expressing PS2 containing N-terminal FLAG epitope were induced for 12 hours and further incubated with media containing 20 µM etoposide. Alternative (34 kDa NTF) and normal (f; 30 kDa) N-terminal cleavage products detected by anti-FLAG antibody and alternative (20K CTF) and endogenous plus normal C-terminal cleavage products (e/f) detected by αPS2Loop were indicated by arrows.

CPP32, the mammalian homologue of CED-3, is activated through a protease cascade in response to apoptotic stimuli, and cleaves specific intracellular substrates during apoptosis (Martin, S. J. and Green, D. R., *Cell* 82:349–352 (1995); Chinnaiyan, A. M. and Dixit, V. M., *Curr. Biol.* 6:555–562 (1996)). Thus, whether the alternative PS2-CTF was generated from full-length 54 kDa PS2 during apoptosis was tested. For this purpose, a relatively low-expressing inducible H4 cell line was used in which low to undetectable levels of the 20 kDa CTF were observed at 12 hours post-induction under normal conditions. When apoptosis was induced with 20 μM etoposide, the alternative 20 kDa CTF as well as the corresponding alternative N-terminal fragment (NTF) were generated (FIG. 8). The alternative NTF was 34 kDa while the "normal" NTF, labeled as band f in the top panel of FIG. 8, was 30 kDa. The alternative PS2 cleavage fragments were first observed at 3 hours post-treatment with etoposide. Treatment with increasing concentrations of zVAD-fmk inhibited the generation of both alternative cleavage products (FIG. 8). These data indicate that full-length PS2 gives rise to the alternative N- and C-terminal cleavage fragments following the induction of apoptosis. However, these data do not exclude the possibility that the 20 kDa CTF might also be generated by cleavage of the 25 kDa CTF.

Figure 9A:
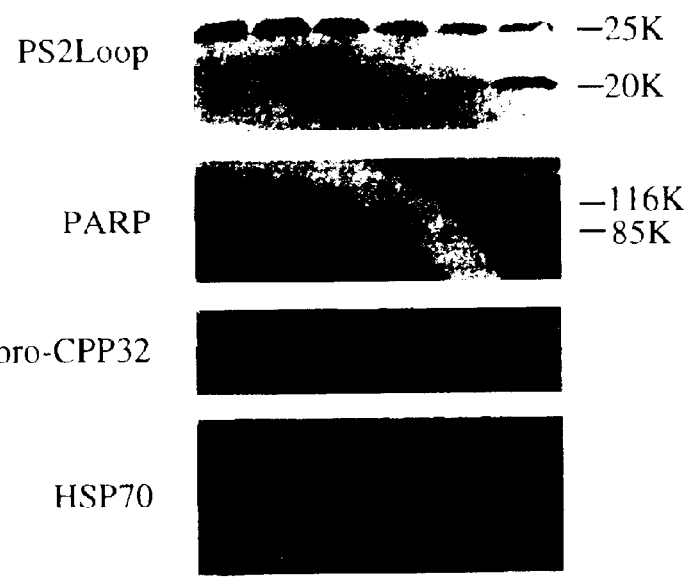
FIG. 9. (a) Cleavage of endogenous PS2 CTF during apoptosis induced by staurosporine (STS). H4 human neuroglioma cells were treated with 1 µM STS for timed intervals indicated on the top panels and lysates were analyzed by Western blotting using αPS2Loop along with antibodies to poly(ADP-ribose) polymerase (PARP), CPP32, and HSP70. (b, c) Inhibition of STS-induced (b) or etoposide-induced (c) cleavage of PS2, PARP, and pro-CPP32 in H4 cells by zVAD-fmk. Cells were pre-treated with inhibitors for 1 hour, further incubated in the presence or absence of 2 μM STS (b) or 20 μM etoposide for 18 hours. and lysates were analyzed by Western blotting. (d) Inhibition of apoptosis-induced cleavage of PS2 by zDEVD-fmk (inhibitor for a CPP32-like protease). (e) Dose-response curves of the effect of zVAD-fmk (Δ) and zDEVD-fmk (o) on STS-induced apoptotic cleavage of PS2. Relative amounts of 20 kDa PS2 fragments from the cells co-treated with 1 μM STS (18 hours) plus either zVAD-fmk or zDEVD-fmk were measured by the transmittance analysis of the Western blot as described (Bush, A. I., et al., Ann. Neurol. 32:57–65 (1992)). The amounts of 20 kDa fragment from the cells treated with STS alone were standardized as 100%. With the exception of (d) (4–20% gradient gel), all SDS-PAGE were performed using 16% gels.

Whether endogenous PS2 is also cleaved by CPP32-like proteases that are activated by apoptotic stimuli was next examined. When untransfected H4 cells were treated with staurosporine, apoptosis was induced (FIG. 9a) as indicated by poly(ADP-ribose) polymerase (PARP) cleavage, proteolysis of inactive CPP32 precursor (pro-CPP32), and decreased viability (assayed by tryphan blue exclusion) (Martin, S. J. and Green, D. R., Cell 82:349–352 (1995); Chinnaiyan, A. M. and Dixit, V. M., Curr. Biol. 6:555–562 (1996)). The progression of apoptosis correlated with the increased generation of the endogenous 20 kDa PS2-CTF and decreased production of the 25 kDa CTF (starting at six hours post-treatment; FIG. 9a).

Figure 9B:
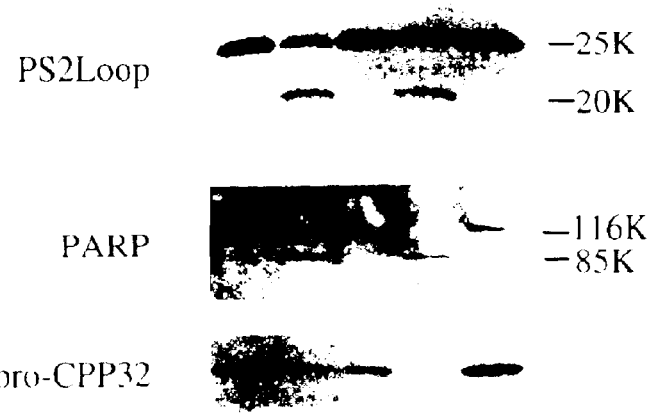
Figure 9E:
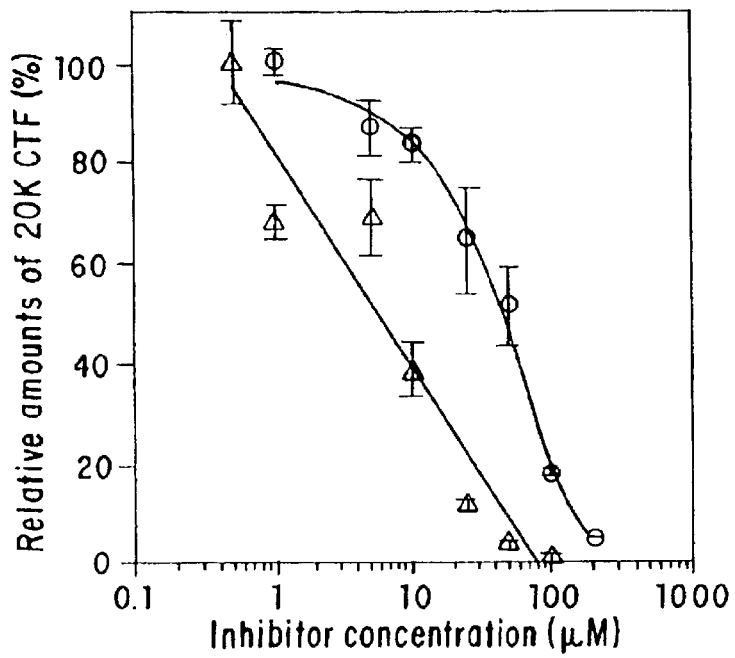

Alternative cleavage of endogenous PS2 during either staurosporine-induced or etoposide-induced apoptosis was specifically blocked by zVAD (FIGS. 9b and 9c) and zDEVD (FIG. 9d), both of which displayed no effect on normal processing of PS2 (the generation of 25 kDa endogenous fragment itself). 25 μM zVAD was as effective as 100 μM zDEVD in inhibiting apoptosis-induced cleavage of PS2 (FIG. 9e). This is most likely due to the fact that zVAD blocks the activation of the upstream protease cascade during the apoptotic pathway, while zDEVD specifically acts downstream as a competitive inhibitor for the CPP32 cleavage site (Martin, S. J. and Green, D. R., Cell 82:349–352 (1995); Chinnaiyan, A. M. and Dixit, V. M., Curr. Biol. 6:555–562 (1996)). These data indicate that in native H4 cells undergoing apoptosis, a CPP32-like protease is responsible for the generation of the 20 kDa PS2-CTF. Thus, like PARP or Lamin A., PS2 appears to serve as an apoptotic death substrate which undergoes alternative proteolysis during apoptosis. In addition, these findings were confirmed in native SK-N-SC neuroblastoma cells.

Figure 10A:
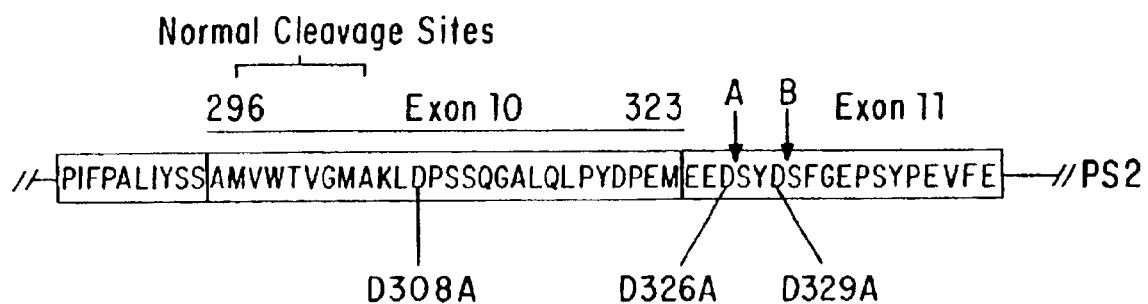
FIG. 10. Abolition of zVAD/zDEVD-sensitive cleavage of PS2 by replacement of Asp-326 or Asp-329. (a) Consensus ICE/Ced-3 protease cleavage sites located after Asp326 or Asp329 (indicated by vertical arrows A and B, respectively) at the PS2 loop domain encoded by exon 11 (SEQ ID NO: 19). Note that normal cleavage sites are located in the distal region encoded by exon 10 (SEQ ID NO: 19) (originally called exon 9) (Perez-Tur, J., et al. NeuroReport 7:297–301 (1995). (b) Effect of D326A and D329A mutations on the generation of the 20 kDa PS2 fragment. Inducible constructs encoding C-terminal FLAG epitope-tagged PS2 with indicated mutations (wild-type, D308A, D326A, and D329A) were transiently transfected into tetracycline-responsive founder H4 cells. Cells were grown in the presence of tetracycline (induction) for 24 hours, and further incubated in the presence of 20 μM etoposide for 9 hours. Samples were then analyzed by Western blotting using αPS2Loop or anti-FLAG.
Figure 10B:
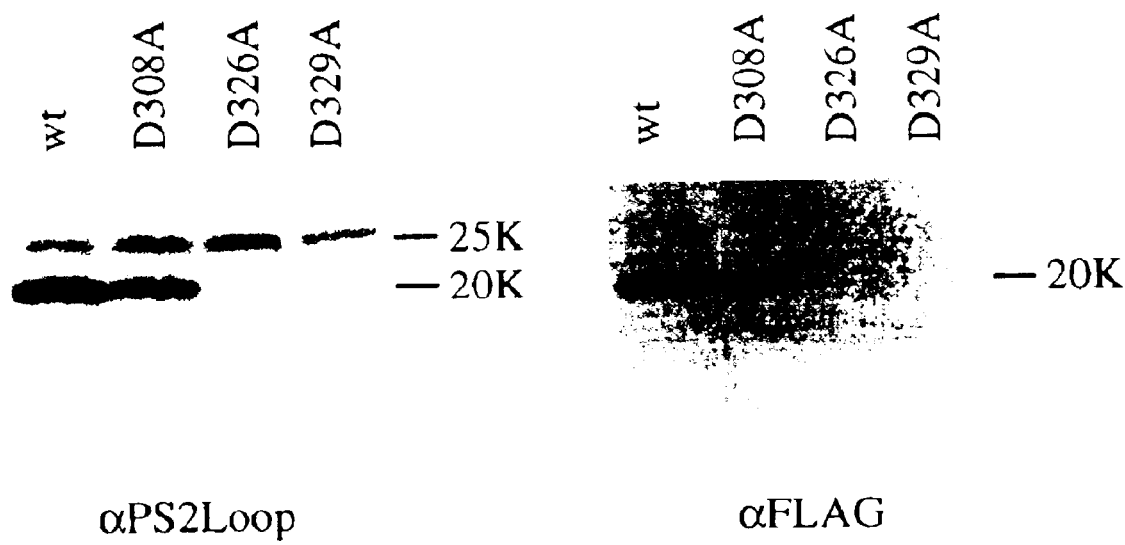

Differential cleavage by apoptotic and non-apoptotic proteases has also been demonstrated for the sterol-regulatory element binding proteins, SREBP-1 and SREBP2, ER proteins which control cellular cholesterol homeostatis. Both SREBP-1 and SREBP-2 have been shown to be cleaved by CPPP32 (Wang, X., et al., EMBO J 15:1012–1020 (1996)) and CPP32-related MCH3 (Pai, J. -T., et al., Proc. Natl. Acad. Sci (USA) 93:5437–5442 (1996)) at the site DSEP DSPVF (SEQ ID NO: 16) for SREBP-1, and the site KDEP DSPPV (SEQ ID NO: 17) for SREBP-2 (Wang, X., et al., EMBO J. 15:1012–1020 (1996)). A potential consensus site (DSYDS, a.a. 326–330 (SEQ ID NO: 1); FIG. 10a) for cleavage by a CPP32-related protease was localized in the large hydrophilic loop following predicted transmembrane domain 6 of PS2, encoded by exon 11 (formerly exon 10) (Perez-Tur, J., et al. NeuroReport 7:297–301 (1995)). To test this site, either of the two Asp residues with Ala (FIG. 10a) were substituted. Both substitutions individually blocked the generation of the 20 kDa CTF (FIG. 10b), indicating that PS2 is most likely cleaved after either the D326 or D329. The presence of D326 might also be required for cleavage following D329 or vice-versa. Meanwhile, the substitution, D308A, had no effect on cleavage. These data demonstrate that a CPP32-like protease most likely cleaves PS2 at the predicted consensus cleavage site (Asp-X) which resides distal to the normal cleavage site to yield the apoptosis-associated PS2-CTF.

Next, whether PS1, a closely related homologue of PS2, also undergoes alternative cleavage when overexpressed and/or during apoptosis was tested. For this purpose, inducible H4 cell lines expressing PS1 with a C-terminal FLAG-epitope tag were established. In cells overexpressing high levels of PS1 (clone IF.22, tet–), high molecular weight forms of PS1, 45 kDa full-length PS1, a 24 kDa "normal" transgene-derived cleavage product (arrow f'), the 23 kDa endogenous CTF (arrow e'), and an additional 14 kDa CTF were observed (FIG. 11a). However, in the clonal cell line expressing lower levels of PS1 (clone IF24), full-length PS1 and the normal CTF were predominantly detected while the alternative 14 kDa CTF fragment was not detectable. As was observed for PS2, the generation of alternative 14 kDa PS1-CTF was blocked in the overexpressing cell lines by treatment with zVAD or zDEVD.

Whether endogenous PS1 is cleaved by CP32-like proteases following induction of apoptosis was also tested. The 23 kDa endogenous PS1 CTF was observed in H4 cells as a doublet presumably due to protein kinase C (PKC)-mediated phosphorylation of the fragment. Induction of apoptosis with staurosporine led to the generation of the 14 kDa PS1-CTF and also blocked the phosphorylation of the endogenous CTF (FIG. 11b). This is consistent with the fact that staurosporine inhibits PKC activity. Etoposide-induced apoptosis also led to the generation of the 14 kDa CTF but, as expected, did not block phosphorylation of the endogenous PS1-CTF (FIG. 11d). As with PS2, apoptosis-associated cleavage of endogenous PS1 was blocked by the treatment with zVAD (FIGS. 11c and 11d) or zDEVD. The size of the alternative PS1-CTF and a scan of the PS1 amino acid sequence suggested that the consensus sequence QRDSH (a.a. 344–348)(SEQ ID NO: 18) is the most likely site for CPP32-related cleavage in PS1 although this will require direct testing.

Figure 12A:
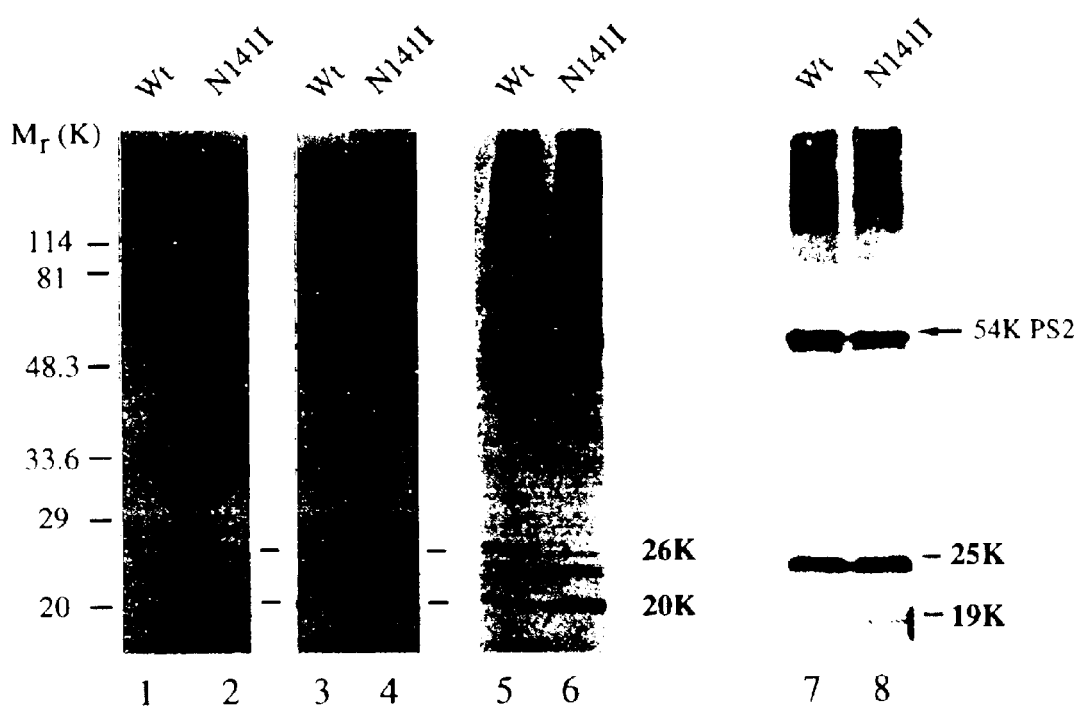
FIG. 12. Relative increase of the 20 kDa PS2 CTF in H4 cells expressing N141I mutant (Volga German) PS2. (a) CTF generated from H4 cells expressing wild-type (lane 1, 3, 5, 7) and N141I FAD mutant (lane 2, 4, 6, 8) PS2 either with C-terminal (lanes 1–6) or N-terminal (lanes 7, 8) FLAG epitope-tag (detected by αPS2Loop). (b) Values (mean±s.d., n=30; *p<0.05) represent ratio of relative amounts of apoptotic fragment (20 kDa CTF) over normal cleavage product (26 kDa CTF) from multiple wild-type and FAD mutant (N141I) PS2 cloned lines induced for 24 hrs. Data from three independent experiments using five different wild-type and mutant PS2 cells are expressed.
Figure 12B:
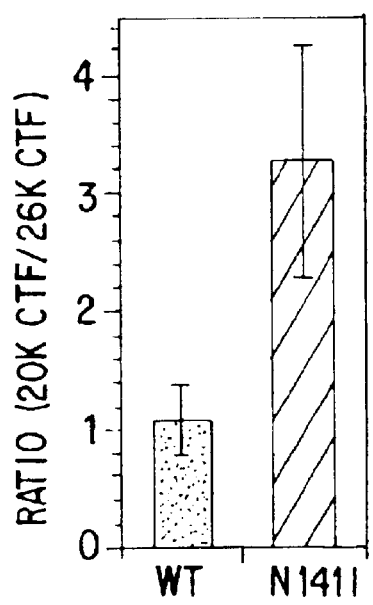

To begin to investigate a potential association between apoptotic PS2 cleavage products and AD pathogenesis, the effect of the N141I Volga German FAD mutation (Levy-Lahud, E., et al., Science 269:973–977 (1995)) on the generation of the 20 kDa PS2-CTF was examined. Multiple inducible cell lines expressing wild-type or FAD mutant (N141I) forms of PS2 were analyzed by Western blotting. In clonal cell lines exhibiting similar levels of transgene expression, the ratio of the 20 kDa CTF:26 kDa CTF was significantly elevated (approximately three-fold) in the PS2-N141I cells relative to the wild-type PS2 cells (FIGS. 12a and 12b). It is interesting to note that huntingtin, a protein associated with another neurodegenerative disorder, Huntington's disease (HD), has also been shown to be cleaved by CPP32 (Goldberg, Y. P., et al., Nature Gen. 13:442–449 (1996)). Thus, it is conceivable that a conformational change in PS2 caused by the N141I FAD mutation contributes to the enhanced susceptibility of PS2 to cleavage mediated by CPP32-like protease.

Apoptotic cell death has been reported to be a pathological feature of AD (Johnson, E. M., Neurobiol. Aging 15:5187–5189 (1994); Cotman, C. W. and Anderson, A. J., Mol. Neurobiol. 10:19–45 (1995); LeBlanc, A., "Apoptosis and Alzheimer's Disease," in Molecular Mechanism of Dementia, Humana Press, Totowa, N.J. (1996), pp. 57–71), although the exact contribution of apoptosis to the pathogenesis of Alzheimer's disease remains unclear. It is possible that the alternative endoproteolytic PS1 and PS2 fragments generated by CPP32-like proteases under apoptotic conditions, may serve as pro-apoptotic effectors which may alter the apoptotic threshold and make cells more vulnerable to apoptosis. The observed increase in apoptotic PS2 fragments in cells overexpressing the FAD mutant PS2-N141I raises the possibility that this fragment may contribute to the report of enhanced susceptibility to apoptosis due to this mutation (Wolozin, B., et al., *Science* 274:1710–1713 (1996); Deng, G., et al., *FEBS Lett.* 397:50–54 (1996)). The N141I FAD mutation in PS2 and other FAD defects in PS1 and PS2 have previously been shown to lead to increased production of AP42 in fibroblasts and plasma of DAD patients as well as in transfected cells and transgenic mice expressing mutant PS genes (Scheuner, D., et al., *Nature Med.* 2:864–870 (1996); Tomita, T., et al, *Proc. Natl. Acad. Sci. (USA)* 94:2025–2030 (1997); Borchelt, D. R., et al., *Neuron* 17:1005–1013 (1995); Citron, M., et al., *Nature Med.* 3:67–72 (1996); Duff, K., et al., *Nature* 383:710–713 (1996)). In addition, treatment of cells with Aβ has also been reported to induce apoptotic neuronal death in vitro (concentrations of 1–100 μM) and in vivo (Johnson, E. M., *Neurobiol. Aging* 15:5187–5189 (1994); Cotman, C. W. and Anderson, A. J., *Mol. Neurobiol.* 10:19–45 (1995); LeBlanc, A., "Apoptosis and Alzheimer's Disease," in *Molecular Mechanism of Dementia*, Humana Press, Totowa, N.J. (1996), pp. 57–71; Yankner, B. A., et al., *Science* 250:279–286 (1990); Forloni, G., et al., *NeuroReport* 4:523–526 (1993); LaFerla, F. M., et al., *Nature Genet.* 9:21–30 (1995)), and to downregulate anti-apoptotic bcl-2 expression in primary neurons (concentration of 100 nM) (Paradis, E., et al., *J. Neurosci.* 16:7533–7539 (1996)). Collectively, these observations suggest at least two potential pathogenic pathways: 1. alternative PS cleavage products may directly participate in inducing pro-apoptotic conditions which in turn lead to pathogenic changes associated with FAD inducing neuronal/synaptic degeneration and subsequent generation of Aβ42; 2. alternative PS cleavage products may induce the increased production or accumulation of Aβ42 which, in turn, effects apoptotic changes and neuronal cell death.

Example 6

Expression of Presenilin 2 (PS2) in a Stable Cell Line

Construction of expression plasmids for wild-type and mutant (N141I, a familial Alzheimer mutation; D329A, an artificial caspase clip site mutation; N141I/D329A, double mutant containing both N141I and D329A mutations) forms of PS2. The generation of expression vectors (in pUHD 10-3 backbone) for PS2-wild-type, PS2N 141I, and PS2-D329A have been previously described (Kim, T -W., et al., *J. Biol. Chem.* 272:11006–11010 (1997); Kim, T -W., et al., *Science* 277:373–376 (1997)). To generate a N141I/D329 variant, the point mutation in the aspartate cleavage site of PS2 (D329A) was introduced into a PS2-N141I open reading frame (ORF) by site-directed mutagenesis using Muta-Gene phagemid kit (Bio-Rad). The resulting plasmids were subcloned into pcDNA3-Zeocin vector (Invitrogen) for the stable transfection.

The Chinese Hamster Ovary (CHO) cells stably expressing human amyloid precursor protein (APP751), termed 7W cells, were previously described (Koo, E. H. & Squazzo S. L., *J. Biol. Chem.* 269:17386–17389 (1994); Xia W., et al., *J. Biol. Chem.* 272:7977–7982 (1997)). The 7W cells were transfected with above mentioned cDNA constructs. Zeocin-resistant colonies were isolated in the presence of 250 ug/ml Zeocin and screened for PS2 expression by Western blot analysis using anti-PS2loop antibodies.

Western blot analysis was performed as described previously (Kim, T -W., et al., *J. Biol Chem.* 272:11006–11010 (1997)).

Western blot analysis of cellular lysates prepared from representative, stably transfected clonal lines are shown in FIG. 13. In samples prepared from stable CHO cells expressing PS2 with N141I/D329A (clone # 3, 5, and 7) or N141I (clone #3, and 6), full-length PS2 (FL) with apparent molecular weight 53 kDa and normal C-terminal fragment (CTF) (FIG. 13, panel (a)). The constructs that were used for the stable transfection were verified by DNA sequencing and further characterized by transient transfection. As shown in the FIG. 13 panel (b), the generation of alternative CTF was abolished in the CHO cells transfected with PS2 containing N141I/D329A mutations.

The abbreviations used are: AD, Alzheimer's disease; FAD, familial Alzeheimer's disease; ER, endoplasmic reticulum; ALLN, N-acetyl-L-leucinal-L-norieucinal; PS1, presenilin 1; PS2; BFA, brefeldin A; Aβ, amyloid β-peptide; HMW-PS2, high molecular mass forms of PS2; PS2-CTF, presenilin 2 C-terminal endoproteolytic fragment; PAGE, polyacrylamide gel electrophoresis; PIPES, 1,4-piperazinediethanesulfonic acid; APP, amyloid β-protein precursor.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An antibody having binding affinity that is specific to a purified 20 kDa presenilin-2 C-terminal fragment (PS2-CTF), wherein the molecular weight of said PS2-CTF is determined by a polyacrylamide gel electrophoresis/western transfer procedure, and wherein said antibody does not bind presenilin-2.

2. A method of detecting 20 kDa PS2-CTF, wherein the molecular weight of said PS2-CTF is determined by a polyacrylamide gel electrophoresis/western transfer procedure, in a sample comprising:

a) contacting said sample with an antibody according to claim 1, under conditions such that immunocomplexes form, and b) detecting the presence of said antibody bound to said polypeptide.

3. A diagnostic kit comprising:
a) a first container means containing the antibody according to claim 1 and
b) a second container means containing a conjugate comprising a binding partner of said antibody and a label.

4. A hybridoma which produces the antibody according to claim 1.

5. A method for screening compounds that inhibit proteolytic processing of presenilin 2 in a cell comprising (a) providing a compound to a cell, wherein the cell proteolytically processes presenilin 2, (b) measuring the amount of 20 kDa presenilin 2 C-terminal fragment (PS2-CTF) produced in said cell, and (c) comparing said amount produced to an amount of PS2-CTF produced in a cell not treated with said compound, wherein a decreased amount of 20 kDa presenilin 2 fragment in said cell treated with said compound as compared to a cell not treated with said compound indicates that said compound inhibits proteolytic processing of presenilin 2 in said cell, wherein the molecular weight of said PS2-CTF is determined by a polyacrylamide gel electrophoresis/western transfer procedure.

6. The method according to claim 5, wherein said amount of 20 kDa presenilin 2 fragment produced in said cell is determined by an ELISA assay using an antibidy specific to the 20 kDa presenilin 2 fragment.

* * * * *

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
  (A) LENGTH: 5 amino acids
  (B) TYPE: amino acid
  (C) STRANDEDNESS: single -continued (D) TOPOLOGY: not relevant (ii) MOLECULE TYPE: peptide (xi) SEQUENCE DESCRIPTION: SEQ ID NO: 1:

Asp Ser Tyr Asp Ser
1               5

(2) INFORMATION FOR SEQ ID NO: 2:

(i) SEQUENCE CHARACTERISTICS:
        (A) LENGTH: 6 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 2:

Pro Glu Met Glu Glu Asp
1               5

(2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 3:

Pro Glu Met Glu Glu Asp Ser Tyr Asp
1               5

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 4:

Pro Glu Met Glu Glu Asp Ser
1               5

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 5:

Pro Glu Met Glu Glu Asp Ser Tyr
1               5

(2) INFORMATION FOR SEQ ID NO: 6:

(i) SEQUENCE CHARACTERISTICS:
        (A) LENGTH: 6 amino acids
        (B) TYPE: amino acid

```
              (C) STRANDEDNESS: single
              (D) TOPOLOGY: not relevant (ii) MOLECULE TYPE: peptide (xi) SEQUENCE DESCRIPTION: SEQ ID NO: 6:

Glu Met Glu Glu Asp Ser
1               5

(2) INFORMATION FOR SEQ ID NO: 7:

(i) SEQUENCE CHARACTERISTICS:
              (A) LENGTH: 7 amino acids
              (B) TYPE: amino acid
              (C) STRANDEDNESS: single
              (D) TOPOLOGY: not relevant (ii) MOLECULE TYPE: peptide (xi) SEQUENCE DESCRIPTION: SEQ ID NO: 7:

Glu Met Glu Glu Asp Ser Tyr
1               5

(2) INFORMATION FOR SEQ ID NO: 8:

(i) SEQUENCE CHARACTERISTICS:
              (A) LENGTH: 8 amino acids
              (B) TYPE: amino acid
              (C) STRANDEDNESS: single
              (D) TOPOLOGY: not relevant (ii) MOLECULE TYPE: peptide (xi) SEQUENCE DESCRIPTION: SEQ ID NO: 8:

Glu Met Glu Glu Asp Ser Tyr Asp
1               5

(2) INFORMATION FOR SEQ ID NO: 9:

(i) SEQUENCE CHARACTERISTICS:
              (A) LENGTH: 6 amino acids
              (B) TYPE: amino acid
              (C) STRANDEDNESS: single
              (D) TOPOLOGY: not relevant (ii) MOLECULE TYPE: peptide (xi) SEQUENCE DESCRIPTION: SEQ ID NO: 9:

Glu Glu Asp Ser Tyr Asp
1               5

(2) INFORMATION FOR SEQ ID NO: 10:

(i) SEQUENCE CHARACTERISTICS:
              (A) LENGTH: 7 amino acids
              (B) TYPE: amino acid
              (C) STRANDEDNESS: single
              (D) TOPOLOGY: not relevant (ii) MOLECULE TYPE: peptide (xi) SEQUENCE DESCRIPTION: SEQ ID NO: 10:

Glu Glu Asp Ser Tyr Asp Ser
1               5

(2) INFORMATION FOR SEQ ID NO: 11:

(i) SEQUENCE CHARACTERISTICS:
              (A) LENGTH: 8 amino acids
```

```
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 11:

Glu Glu Asp Ser Tyr Asp Ser Phe
1               5

(2) INFORMATION FOR SEQ ID NO: 12:

(i) SEQUENCE CHARACTERISTICS:
        (A) LENGTH: 6 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 12:

Glu Asp Ser Tyr Asp Ser
1               5

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 13:

Glu Asp Ser Tyr Asp Ser Phe
1               5

(2) INFORMATION FOR SEQ ID NO: 14:

(i) SEQUENCE CHARACTERISTICS:
        (A) LENGTH: 8 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 14:

Glu Asp Ser Tyr Asp Ser Phe Gly
1               5

(2) INFORMATION FOR SEQ ID NO: 15:

(i) SEQUENCE CHARACTERISTICS:
        (A) LENGTH: 8 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 15:

Asp Tyr Lys Asp Asp Asp Asp Lys
1               5

(2) INFORMATION FOR SEQ ID NO: 16:

(i) SEQUENCE CHARACTERISTICS:
```

```
        (A) LENGTH: 9 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 16:

Asp Ser Glu Pro Asp Ser Pro Val Phe
1               5

(2) INFORMATION FOR SEQ ID NO: 17:

(i) SEQUENCE CHARACTERISTICS:
        (A) LENGTH: 9 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 17:

Lys Asp Glu Pro Asp Ser Pro Pro Val
1               5

(2) INFORMATION FOR SEQ ID NO: 18:

(i) SEQUENCE CHARACTERISTICS:
        (A) LENGTH: 5 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 18:

Gln Arg Asp Ser His
1               5

(2) INFORMATION FOR SEQ ID NO: 19:

(i) SEQUENCE CHARACTERISTICS:
        (A) LENGTH: 5 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 19:

Pro Ile Phe Pro Ala Leu Ile Tyr Ser Ser Ala Met Val Trp Thr Val
1               5                   10                  15

Gly Met Ala Lys Leu Asp Pro Ser Ser Gln Gly Ala Leu Gln Leu Pro
            20                  25                  30

Tyr Asp Pro Glu Met Glu Glu Asp Ser Tyr Asp Ser Phe Gly Glu Pro
            35                  40                  45

Ser Tyr Pro Glu Val Phe Glu
```